US011065313B2

(12) United States Patent
King et al.

(10) Patent No.: US 11,065,313 B2
(45) Date of Patent: Jul. 20, 2021

(54) MODIFIED YEAST-BRACHYURY IMMUNOTHERAPEUTIC COMPOSITIONS

(71) Applicants: GLOBEIMMUNE, INC., Louisville, CO (US); THE UNITED STATES OF AMERICA, as represented by the secretary, DEPARTMENT OF HEALTH AND HUMAN SERVICES, Bethesda, MD (US)

(72) Inventors: Thomas H. King, Denver, CO (US); Zhimin Guo, Superior, CO (US); Jeffrey Schlom, Potomac, MD (US); Claudia Palena, Potomac, MD (US)

(73) Assignees: GlobeImmune, Inc., Louisville, CO (US); The USA, as represented by the Secretary, Dept. of Health and Human Services, Bethesda, MD (US)

( * ) Notice: Subject to any disclaimer, the term of this patent is extended or adjusted under 35 U.S.C. 154(b) by 598 days.

(21) Appl. No.: 15/749,832

(22) PCT Filed: Aug. 1, 2016

(86) PCT No.: PCT/US2016/044977
§ 371 (c)(1),
(2) Date: Feb. 2, 2018

(87) PCT Pub. No.: WO2017/023840
PCT Pub. Date: Feb. 9, 2017

(65) Prior Publication Data
US 2018/0214525 A1 Aug. 2, 2018

Related U.S. Application Data

(60) Provisional application No. 62/200,497, filed on Aug. 3, 2015.

(51) Int. Cl.
| *A61K 39/00* | (2006.01) |
| *C07K 14/82* | (2006.01) |
| *A61K 36/06* | (2006.01) |
| *A61P 35/00* | (2006.01) |

(52) U.S. Cl.
CPC .......... *A61K 39/0005* (2013.01); *A61K 36/06* (2013.01); *A61K 39/0011* (2013.01); *A61P 35/00* (2018.01); *C07K 14/82* (2013.01); *A61K 2039/51* (2013.01); *A61K 2039/521* (2013.01); *A61K 2039/523* (2013.01); *A61K 2039/53* (2013.01); *A61K 2039/57* (2013.01); *A61K 2039/585* (2013.01); *A61K 2039/6006* (2013.01)

(58) Field of Classification Search
CPC .................. A61K 39/011; A61K 36/06; A61K 2039/6006; A61K 2039/51; A61K 2039/585; A61K 36/062; A61K 36/064; A61K 2039/52; A61K 2039/523
See application file for complete search history.

(56) References Cited

U.S. PATENT DOCUMENTS

| 4,775,622 | A | 10/1988 | Hitzeman et al. |
| 5,234,830 | A | 8/1993 | Oshima et al. |
| 5,310,654 | A | 5/1994 | Isberg et al. |
| 5,413,914 | A | 5/1995 | Franzusoff |
| 5,830,463 | A | 11/1998 | Duke et al. |
| 5,858,378 | A | 1/1999 | Bostwick |
| 5,919,651 | A | 7/1999 | Hitzeman et al. |
| 6,410,026 | B1 | 6/2002 | Srivastava |
| 7,083,787 | B2 | 8/2006 | Duke et al. |
| 7,175,839 | B1 | 2/2007 | Hiserodt |
| 7,439,042 | B2 | 10/2008 | Duke et al. |
| 7,465,454 | B2 | 12/2008 | Franzusoff et al. |
| 9,198,941 | B2 | 12/2015 | Palena et al. |
| 9,623,097 | B2 | 4/2017 | Palena et al. |
| 2002/0044948 | A1 | 4/2002 | Samir et al. |
| 2003/0035810 | A1 | 2/2003 | Caplan |
| 2006/0009404 | A1 | 1/2006 | Williams |
| 2007/0172503 | A1 | 7/2007 | Selitrennikoff et al. |
| 2007/0224208 | A1 | 9/2007 | Guo et al. |
| 2008/0003239 | A1 | 1/2008 | Duke et al. |
| 2010/0034840 | A1 | 2/2010 | Apelian et al. |
| 2010/0055121 | A1 | 3/2010 | Schlom et al. |
| 2010/0111912 | A1 | 5/2010 | Apelian et al. |
| 2010/0189749 | A1 | 7/2010 | Franzusoff et al. |
| 2011/0229524 | A1 | 9/2011 | Fritsche et al. |
| 2011/0256098 | A1 | 10/2011 | Apelian et al. |
| 2012/0321664 | A1 | 12/2012 | Bellgrau et al. |
| 2016/0271238 | A1 | 9/2016 | Rodell et al. |
| 2017/0246276 | A1 | 8/2017 | Palena et al. |

(Continued)

FOREIGN PATENT DOCUMENTS

| EP | 0414404 | 2/1991 |
| FR | 2486400 | 1/1982 |
| WO | WO 2007/008780 | 1/2007 |

(Continued)

OTHER PUBLICATIONS

Nanni et al, Cancer Research, 2007, vol. 67, p. 11037-11044 (Year: 2007).*
Bachman et al., "Recall proliferation potential of memory CD8+ T cells and antiviral protection," Journal of Immunology, 2005, vol. 175, pp. 4677-4685.
Bizzini et al. "Use of live *Saccharomyces cerevisiae* cells as a biological response modifier in experimental infections," FEMS Microbiology Immunology, 1990, vol. 64, pp. 155-168.
Brake et al. "alpha-Factor-directed synthesis and secretion of mature foreign proteins in Saccharomyces cerevisiae," Proceedings of the National Academy of Sciences USA, Aug. 1984, vol. 81, pp. 4642-4646.
Chugh et al. "Chordoma: The Nonsarcoma Primary Bone Tumor," The Oncologist, Nov. 2007, vol. 12, No. 11, pp. 1344-1350.

(Continued)

Primary Examiner — Karen A. Canella
(74) Attorney, Agent, or Firm — Sheridan Ross P.C.

(57) ABSTRACT

Disclosed are improved yeast-based immunotherapeutic compositions comprising modified Brachyury antigens, and methods for the prevention and/or treatment of cancers characterized by the expression or overexpression of Brachyury.

10 Claims, 2 Drawing Sheets
Specification includes a Sequence Listing.

(56) References Cited

U.S. PATENT DOCUMENTS

| | | |
|---|---|---|
| 2019/0374624 A1 | 12/2019 | Palena et al. |
| 2020/0046818 A1 | 2/2020 | Rodell et al. |

FOREIGN PATENT DOCUMENTS

| | | | |
|---|---|---|---|
| WO | WO 2007/092792 | 8/2007 | |
| WO | WO 2007/133835 | 11/2007 | |
| WO | WO 2008/106551 | 9/2008 | |
| WO | WO-2009042642 A2 * | 4/2009 | .......... G01N 33/505 |
| WO | WO 2010/065626 | 6/2010 | |
| WO | WO 2010/121180 | 10/2010 | |
| WO | WO 2011/115914 | 9/2011 | |
| WO | WO 2012/019127 | 2/2012 | |
| WO | WO 2012/083302 | 6/2012 | |
| WO | WO 2012/109404 | 8/2012 | |
| WO | WO-2012125998 A1 * | 9/2012 | ................ A61P 1/18 |
| WO | WO 2012/174220 | 12/2012 | |
| WO | WO 2013/025972 | 2/2013 | |
| WO | WO-2014186047 A1 * | 11/2014 | ......... A61K 39/0011 |

OTHER PUBLICATIONS

Di Maio et al. "Current comprehensive management of cranial base chordomas: 10-year meta-analysis of observational studies," Journal of Neurosurgery, Dec. 2011, vol. 115, No. 6, pp. 1094-1105.

Efferson et al., "Stimulation of human T cells by an influenza a vector expressing a CTL epitope from the HER-2/neu protooncogene results in higher numbers of antigen-specific TCRhi cells than stimulation with peptide. Divergent roles of IL-2 and IL-15," Anticancer research, 2005, vol. 25, pp. 715-724.

Eto et al., "Immunization with recombinant Escherichia coli expressing retinal S-antigen-induced experimental autoimmune uveitis (EAU) in Lewis rats", Cellular Immunology, vol. 147, No. 1 Mar. 1993, pp. 203-214.

Ferraresi et al. "Chordoma: clinical characteristics, management and prognosis of a case series of 25 patients," BMC Cancer, Jan. 2010, vol. 10, 10 pages.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

Hamilton et al., "High levels of expression of the transcription factor Brachyury induce resistance of human carcinoma cells to immune-mediated attack," Journal for ImmunoTherapy of Cancer, 2013, vol. 1, Suppl. 1, p. P152.

Hamilton et al. Immunological targeting of tumor cells undergoing an epithelial-mesenchymal transition via a recombinant brachyury-yeast vaccine, Oncotarget, Oct. 2013, vol. 4, No. 10, pp. 1777-1790.

Heery et al., "Phase I Trial of a Yeast-Based Therapeutic Cancer Vaccine (GI-6301) Targeting the Transcription Factor Brachyury," Cancer Immunology Research, 2015, vol. 3, Iss. 11, pp. 1248-1256.

Holz et al., "A micro-scale process for high-throughput expression of cDNAs in the yeast Saccharomyces cerevisiae," Protein Expression and Purification, 2002, vol. 25, Iss. 3, pp. 372-378.

Hsu et al., "Generation of chordoma cell line JHC7 and the identification of Brachyury as a novel molecular target: Laboratory investigation," Journal of Neurosurgery, 2011, vol. 115, No. 4, pp. 760-769.

Jambhekar et al., "Revisiting Chordoma With Brachyury, a "New Age" Marker: Analysis of a Validation Study on 51 Cases," Archives of Pathology & Laboratory Medicine, 2010, vol. 134, Iss. 8, pp. 1181-1187.

Kilic et al. "Brachyury expression predicts poor prognosis at early stages of colorectal cancer." European Journal of Cancer, May 2011, vol. 47, No. 7, pp. 1080-1085.

Klepfer et al. "Characterization of rabies glycoprotein expressed in yeast," Archives of Virology, 1993, vol. 128, pp. 269-286.

Launay et al. "Efficacy of epidermal growth factor receptor targeting in advanced chordoma: case report and literature review," BMC Cancer, Oct. 2011, vol. 11, 4 pages.

Lu, et al., "Mutation-Selective Tumor Remission with Ras-Targeted, Whole Yeast-Based Immunotherapy," Cancer Research, 2004, vol. 64, pp. 5084-5088.

Moore et al., "Novel yeast-based vaccine against HIV-SF2 gp160 promotes a cytotoxic 43-62 cell response." FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.

Mosolits et al., "Therapeutic vaccination in patients with gastrointestinal malignancies. A review of immunological and clinical results," Annals of Oncology, 2005, vol. 16, Iss. 6, pp. 847-862.

Nelson et al., "An integrated functional genomics approach identifies the regulatory network directed by brachyury (T) in chordoma," Journal of Pathology, 2012, vol. 228, Iss. 3, pp. 274-285.

Palena et al., "Brachyury, a driver of tumor invasiveness and resistance to multiple therapies, is a novel immunotherapy target," Journal for ImmunoTherapy of Cancer, 2013, vol. 1, Suppl. 1, p. P230.

Palena et al., "Chapter Two—Immune Targeting of Tumor Epithelial-Mesenchymal Transition via Brachyury-Based Vaccines," Advances in Cancer Research, 2015, vol. 128, pp. 69-93.

Palena et al. "The Human T-Box Mesodermal Transcription Factor Brachyury Is a Candidate Target for T-Cell-Mediated Cancer Immunotherapy," Clinical Cancer Research, Apr. 15, 2007, vol. 13, No. 8, pp. 2471-2478.

Pamir et al. "Tumor-biology and current treatment of skull-base chordomas," Advances and Technical Standards in Neurosurgery, Edited by J.D. Pickard, 2008, vol. 33, pp. 36-129.

Romeo et al., "Brachyury and chordoma: the chondroid-chordoid dilemma resolved?," The Journal of Pathology, 2006, vol. 209, Iss. 2, pp. 143-146.

Sadanaga et al., "Dendritic Cell Vaccination with MAGE Peptide Is a Novel Therapeutic Approach for Gastrointestinal Carcinomas," Clinical Cancer Research, 2001, vol. 7, Iss. 8, pp. 2277-2284.

Schreuder et al. "Yeast expressing hepatitis B virus surface antigen determinants on its surface: implications fora possible oral vaccine," Vaccine, Apr. 1996, vol. 14, No. 5, pp. 383-388.

Schwab et al., "Chordoma and chondrosarcoma gene profile: implications for immunotherapy," Cancer Immunology, Immunotherapy, 2009, vol. 58, Iss. 3, pp. 339-349.

Sinai et al. "Enhancement of Resistance to Infectious Diseases by Oral Administration of Brewer's Yeast," Infection and Immunity, May 1974, vol. 9, No. 5, pp. 781-787.

Staab et al., "Spot-Scanning-Based Proton Therapy for Extracranial Chordoma," International Journal of Radiation Oncology * Biology * Physics, 2011, vol. 81, Iss. 4, pp. e489-e496.

Stacchiotti et al. "Systemic Therapy Options for Unresectable and Metastatic Chordomas," Current Oncology Reports, Aug. 2011, vol. 13, No. 4, pp. 323-330.

Stirnimann et al., "Structural Basis of TBX5-DNA Recognition: The T-Box Domain in Its DNA-Bound and -Unbound Form," Journal of Molecular Biology, 2010, vol. 400, Iss. 1, pp. 71-81.

Stubbs, et al., "Whole Recombinant Yeast Vaccine Activates Dendritic Cells and Elicits Protective Cell-Mediated Immunity," National Medicine, May 2001, vol. 7, No. 5, pp. 1-5.

Tsang et al., "The generation and analysis of a novel combination of recombinant adenovirus vaccines targeting three tumor antigens as an immunotherapeutic," Journal for ImmunoTherapy of Cancer, 2015, vol. 3, Suppl. 2, p. P452.

Tucker et al., "Identification and characterization of a cytotoxic T-lymphocyte agonist epitope of brachyury, a transcription factor

(56) References Cited

OTHER PUBLICATIONS involved in epithelial to mesenchymal transition and metastasis," Cancer Immunology, Immunotherapy, 2014, vol. 63, Iss. 12, pp. 1307-1317.
Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.
Walcott et al. "Chordoma: current concepts, management, and future directions," The Lancet Oncology, Feb. 2012, vol. 13, pp. e69-e76.
Wheeler, "Preventive vaccines for cervical cancer," Salud p'ublica de M'exico, 1997, vol. 39, pp. 283-287.
Yang et al. "Corroboration of a familial chordoma locus on chromosome 7q and evidence of genetic heterogeneity using single nucleotide polymorphisms (SNPs)," International Journal of Cancer, Sep. 2005, vol. 116, No. 3, pp. 487-491.
Yoshiyuki et al., "Extremely simple, rapid and highly efficient transformation method for the yeast *Saccharomyces cerevisiae* using glutathione and early log phase cells," Journal of Bioscience and Bioengineering, 2002, vol. 94, Iss. 2, pp. 166-171. (Abstract only).
International Preliminary Report on Patentability for International (PCT) Patent Application No. PCT/US2016/044977 dated Feb. 15, 2018, 11 pages.
Official Action for European Patent Application No. 16750335.8 dated Oct. 23, 2019, 8 pages.
International Search Report issued by the European Patent Office for International Patent Application No. PCT/US2016/044977, dated Nov. 3, 2016, 9 pages.
Written Opinion issued by the European Patent Office for International Patent Application No. PCT/US2016/044977, dated Nov. 3, 2016, 10 pages.

Reis E Sousa et al. "Conditioning of Dendritic Cells by Pathogen-Derived Stimuli," Immunobiology, 2001, vol. 204, Iss. 5, pp. 595-597.
Hayama et al., "Extremely simple, rapid and highly efficient transformation method for the yeast *Saccharomyces cerevisiae* using glutathione and early log phase cells," Journal of Bioscience and Bioengineering, 2002, vol. 94, Iss. 2, pp. 166-171. (Abstract only).
Official Action for European Patent Application No. 16750335.8 dated Mar. 1, 2019, 9 pages.
Notice of Acceptance for Australian Patent Application No. 2016303525 dated Jan. 6, 2021, 3 pages.
Donahue et al., "Identification of tumor associated immune responses against brachyury, a transcription factor and driver of EMT, in chordoma patients receiving a yeast-brachyury vaccine (gi-6301)," Journal for ImmunoTherapy of Cancer, Nov. 2014, vol. 2(Suppl 3), p. 148 (2 pages).
Official Action (English translation) for Chinese Patent Application No. 201680056316.X dated Jan. 14, 2021, 9 pages.
Notice of Allowance for European Patent Application No. 16750335.8 dated Oct. 22, 2020, 7 pages.
Notice of Allowance (with English translation) for Japanese Patent Application No. 2018-505476 dated Oct. 6, 2020, 6 pages.
Müller et al., "Crystallographic structure of the T domain—DNA complex of the Brachyury transcription factor", Nature, 1997, vol. 389, pp. 884-888.
Official Action for Australian Patent Application No. 2016303525 dated Jun. 15, 2020, 4 pages.
Official Action for European Patent Application No. 16750335.8 dated Apr. 30, 2020, 7 pages.
Official Action (with English translation) for Japanese Patent Application No. 2018-505476 dated Jun. 23, 2020, 10 pages.
Official Action (with English translation) for Taiwanese Patent Application No. 105124349, dated Apr. 15, 2021, 13 pages.
Official Action (with English translation) for Israel Patent Application No. 257208 dated Feb. 25, 2021, 7 pages.

* cited by examiner

SEQUENCE LISTING

<160> NUMBER OF SEQ ID NOS: 16

<210> SEQ ID NO 1
<211> LENGTH: 2518
<212> TYPE: DNA
<213> ORGANISM: Homo sapiens
<220> FEATURE:
<221> NAME/KEY: CDS
<222> LOCATION: (494)..(1801)

<400> SEQUENCE: 1

```
tttgcttttg cttatttccg tccatttccc tctctgcgcg cggaccttcc ttttccagat    60
ggtgagagcc gcggggacac ccgacgccgg ggcaggctga tccacgatcc tgggtgtgcg   120
taacgccgcc tggggctccg tgggcgaggg acgtgtgggg acaggtgcac cggaaactgc   180
cagactggag agttgaggca tcggaggcgc gagaacagca ctactactgc ggcgagacga   240
gcgcggcgca tcccaaagcc cggccaaatg cgctcgtccc tgggagggga gggaggcgcg   300
cctggagcgg ggacagtctt ggtccgcgcc ctcctcccgg gtctgtgccg gacccggga   360 cccgggagcc gtcgcaggtc tcggtccaag gggccccttt tctcggaagg gcggcggcca   420
agagcaggga aggtggatct caggtagcga gtctgggctt cggggacggc ggggagggga   480
gccggacggg agg atg agc tcc cct ggc acc gag agc gcg gga aag agc      529
              Met Ser Ser Pro Gly Thr Glu Ser Ala Gly Lys Ser
                1               5                  10 ctg cag tac cga gtg gac cac ctg ctg agc gcc gtg gag aat gag ctg    577
Leu Gln Tyr Arg Val Asp His Leu Leu Ser Ala Val Glu Asn Glu Leu
         15                  20                  25 cag gcg ggc agc gag aag ggc gac ccc aca gag cgc gaa ctc cgc gtg    625
Gln Ala Gly Ser Glu Lys Gly Asp Pro Thr Glu Arg Glu Leu Arg Val
     30                  35                  40 ggc ctg gag gag agc gag ctg tgg ctg cgc ttc aag gag ctc acc aat    673
Gly Leu Glu Glu Ser Glu Leu Trp Leu Arg Phe Lys Glu Leu Thr Asn
 45                  50                  55                  60 gag atg atc gtg acc aag aac ggc agg agg atg ttt ccg gtg ctg aag    721
Glu Met Ile Val Thr Lys Asn Gly Arg Arg Met Phe Pro Val Leu Lys
                 65                  70                  75 gtg aac gtg tct ggc ctg gac ccc aac gcc atg tac tcc ttc ctg ctg    769
Val Asn Val Ser Gly Leu Asp Pro Asn Ala Met Tyr Ser Phe Leu Leu
             80                  85                  90 gac ttc gtg gcg gcg gac aac cac cgc tgg aag tac gtg aac ggg gaa    817
Asp Phe Val Ala Ala Asp Asn His Arg Trp Lys Tyr Val Asn Gly Glu
         95                 100                 105 tgg gtg ccg ggg ggc aag ccg gag ccg cag gcg ccc agc tgc gtc tac    865
```

-continued

```
Trp Val Pro Gly Gly Lys Pro Glu Pro Gln Ala Pro Ser Cys Val Tyr
    110             115                 120 atc cac ccc gac tcg ccc aac ttc ggg gcc cac tgg atg aag gct ccc      913
Ile His Pro Asp Ser Pro Asn Phe Gly Ala His Trp Met Lys Ala Pro
125             130                 135                 140 gtc tcc ttc agc aaa gtc aag ctc acc aac aag ctc aac gga ggg ggc      961
Val Ser Phe Ser Lys Val Lys Leu Thr Asn Lys Leu Asn Gly Gly Gly
            145                 150                 155 cag atc atg ctg aac tcc ttg cat aag tat gag cct cga atc cac ata     1009
Gln Ile Met Leu Asn Ser Leu His Lys Tyr Glu Pro Arg Ile His Ile
        160                 165                 170 gtg aga gtt ggg ggt cca cag cgc atg atc acc agc cac tgc ttc cct     1057
Val Arg Val Gly Gly Pro Gln Arg Met Ile Thr Ser His Cys Phe Pro
    175                 180                 185 gag acc cag ttc ata gcg gtg act gct tat cag aac gag gag atc aca     1105
Glu Thr Gln Phe Ile Ala Val Thr Ala Tyr Gln Asn Glu Glu Ile Thr
190                 195                 200 gct ctt aaa att aag tac aat cca ttt gca aaa gct ttc ctt gat gca     1153
Ala Leu Lys Ile Lys Tyr Asn Pro Phe Ala Lys Ala Phe Leu Asp Ala
205                 210                 215                 220 aag gaa aga agt gat cac aaa gag atg atg gag gaa ccc gga gac agc     1201
Lys Glu Arg Ser Asp His Lys Glu Met Met Glu Glu Pro Gly Asp Ser
            225                 230                 235 cag caa cct ggg tac tcc caa tgg ggg tgg ctt ctt cct gga acc agc     1249
Gln Gln Pro Gly Tyr Ser Gln Trp Gly Trp Leu Leu Pro Gly Thr Ser
        240                 245                 250 acc ctg tgt cca cct gca aat cct cat cct cag ttt gga ggt gcc ctc     1297
Thr Leu Cys Pro Pro Ala Asn Pro His Pro Gln Phe Gly Gly Ala Leu
    255                 260                 265 tcc ctc ccc tcc acg cac agc tgt gac agg tac cca acc ctg agg agc     1345
Ser Leu Pro Ser Thr His Ser Cys Asp Arg Tyr Pro Thr Leu Arg Ser
270                 275                 280 cac cgg tcc tca ccc tac ccc agc ccc tat gct cat cgg aac aat tct     1393
His Arg Ser Ser Pro Tyr Pro Ser Pro Tyr Ala His Arg Asn Asn Ser
285                 290                 295                 300 cca acc tat tct gac aac tca cct gca tgt tta tcc atg ctg caa tcc     1441
Pro Thr Tyr Ser Asp Asn Ser Pro Ala Cys Leu Ser Met Leu Gln Ser
            305                 310                 315 cat gac aat tgg tcc agc ctt gga atg cct gcc cat ccc agc atg ctc     1489
His Asp Asn Trp Ser Ser Leu Gly Met Pro Ala His Pro Ser Met Leu
        320                 325                 330 ccc gtg agc cac aat gcc agc cca cct acc agc tcc agt cag tac ccc     1537
Pro Val Ser His Asn Ala Ser Pro Pro Thr Ser Ser Ser Gln Tyr Pro
    335                 340                 345 agc ctg tgg tct gtg agc aac ggc gcc gtc acc ccg ggc tcc cag gca     1585
Ser Leu Trp Ser Val Ser Asn Gly Ala Val Thr Pro Gly Ser Gln Ala
350                 355                 360 gca gcc gtg tcc aac ggg ctg ggg gcc cag ttc ttc cgg ggc tcc ccc     1633
Ala Ala Val Ser Asn Gly Leu Gly Ala Gln Phe Phe Arg Gly Ser Pro
365                 370                 375                 380 gcg cac tac aca ccc ctc acc cat ccg gtc tcg gcg ccc tct tcc tcg     1681
Ala His Tyr Thr Pro Leu Thr His Pro Val Ser Ala Pro Ser Ser Ser
            385                 390                 395 gga tcc cca ctg tac gaa ggg gcg gcc gcg gcc aca gac atc gtg gac     1729
Gly Ser Pro Leu Tyr Glu Gly Ala Ala Ala Ala Thr Asp Ile Val Asp
        400                 405                 410 agc cag tac gac gcc gca gcc caa ggc cgc ctc ata gcc tca tgg aca     1777
Ser Gln Tyr Asp Ala Ala Ala Gln Gly Arg Leu Ile Ala Ser Trp Thr
415                 420                 425
```

```
cct gtg tcg cca cct tcc atg tga agcagcaagg cccaggtccc gaaagatgca    1831
Pro Val Ser Pro Pro Ser Met
    430             435 gtgactttt  gtcgtggcag ccagtggtga ctggattgac ctactaggta cccagtggca    1891
gtctcaggtt aagaaggaaa tgcagcctca gtaacttcct tttcaaagca gtggaggagc    1951
acacggcacc tttccccaga gccccagcat cccttgctca cacctgcagt agcggtgctg    2011
tcccaggtgg cttacagatg aacccaactg tggagatgat gcagttggcc caacctcact    2071
gacggtgaaa aaatgtttgc cagggtccag aaacttttt  tggtttattt ctcatacagt    2131
gtattggcaa ctttggcaca ccagaatttg taaactccac cagtcctact ttagtgagat    2191
aaaaagcaca ctcttaatct tcttccttgt tgctttcaag tagttagagt tgagctgtta    2251
aggacagaat aaaatcatag ttgaggacag caggtttag  ttgaattgaa aatttgactg    2311
ctctgccccc tagaatgtgt gtattttaag catatgtagc taatctcttg tgttgttaaa    2371
ctataactgt ttcatatttt tcttttgaca aagtagccaa agacaatcag cagaaagcat    2431
tttctgcaaa ataaacgcaa tatgcaaaat gtgattcgtc cagttattag tgaagcccct    2491 cctttgtga gtatttactg tttattg                                        2518
```

<210> SEQ ID NO 2
<211> LENGTH: 435
<212> TYPE: PRT
<213> ORGANISM: Homo sapiens

<400> SEQUENCE: 2

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
```

```
                    225                 230                 235                 240
                Tyr Ser Gln Trp Gly Trp Leu Leu Pro Gly Thr Ser Thr Leu Cys Pro
                                    245                 250                 255

Pro Ala Asn Pro His Pro Gln Phe Gly Gly Ala Leu Ser Leu Pro Ser
                                    260                 265                 270

Thr His Ser Cys Asp Arg Tyr Pro Thr Leu Arg Ser His Arg Ser Ser
                                    275                 280                 285

Pro Tyr Pro Ser Pro Tyr Ala His Arg Asn Asn Ser Pro Thr Tyr Ser
                                    290                 295                 300

Asp Asn Ser Pro Ala Cys Leu Ser Met Leu Gln Ser His Asp Asn Trp
                305                 310                 315                 320

Ser Ser Leu Gly Met Pro Ala His Pro Ser Met Leu Pro Val Ser His
                                    325                 330                 335

Asn Ala Ser Pro Pro Thr Ser Ser Ser Gln Tyr Pro Ser Leu Trp Ser
                                    340                 345                 350

Val Ser Asn Gly Ala Val Thr Pro Gly Ser Gln Ala Ala Ala Val Ser
                                    355                 360                 365

Asn Gly Leu Gly Ala Gln Phe Phe Arg Gly Ser Pro Ala His Tyr Thr
                                    370                 375                 380

Pro Leu Thr His Pro Val Ser Ala Pro Ser Ser Ser Gly Ser Pro Leu
                385                 390                 395                 400

Tyr Glu Gly Ala Ala Ala Thr Asp Ile Val Asp Ser Gln Tyr Asp
                                    405                 410                 415

Ala Ala Ala Gln Gly Arg Leu Ile Ala Ser Trp Thr Pro Val Ser Pro
                                    420                 425                 430

Pro Ser Met
                        435

<210> SEQ ID NO 3
<211> LENGTH: 1305
<212> TYPE: DNA
<213> ORGANISM: Homo sapiens
<220> FEATURE:
<221> NAME/KEY: CDS
<222> LOCATION: (1)..(1305)

<400> SEQUENCE: 3 atg agc tcc cct ggc acc gag agc gcg gga aag agc ctg cag tac cga     48
Met Ser Ser Pro Gly Thr Glu Ser Ala Gly Lys Ser Leu Gln Tyr Arg
1               5                   10                  15 gtg gac cac ctg ctg agc gcc gtg gag aat gag ctg cag gcg ggc agc     96
Val Asp His Leu Leu Ser Ala Val Glu Asn Glu Leu Gln Ala Gly Ser
                20                  25                  30 gag aag ggc gac ccc aca gag cgc gaa ctg cgc gtg ggc ctg gag gag    144
Glu Lys Gly Asp Pro Thr Glu Arg Glu Leu Arg Val Gly Leu Glu Glu
            35                  40                  45 agc gag ctg tgg ctg cgc ttc aag gag ctc acc aat gag atg atc gtg    192
Ser Glu Leu Trp Leu Arg Phe Lys Glu Leu Thr Asn Glu Met Ile Val
        50                  55                  60 acc aag aac ggc agg agg atg ttt ccg gtg ctg aag gtg aac gtg tct    240
Thr Lys Asn Gly Arg Arg Met Phe Pro Val Leu Lys Val Asn Val Ser
65                  70                  75                  80 ggc ctg gac ccc aac gcc atg tac tcc ttc ctg ctg gac ttc gtg gcg    288
Gly Leu Asp Pro Asn Ala Met Tyr Ser Phe Leu Leu Asp Phe Val Ala
                85                  90                  95 gcg gac aac cac cgc tgg aag tac gtg aac ggg gaa tgg gtg ccg ggg    336
Ala Asp Asn His Arg Trp Lys Tyr Val Asn Gly Glu Trp Val Pro Gly
                100                 105                 110
```

| | | |
|---|---|---|
| ggc aag ccg gag ccg cag gcg ccc agc tgc gtc tac atc cac ccc gac<br>Gly Lys Pro Glu Pro Gln Ala Pro Ser Cys Val Tyr Ile His Pro Asp<br>115                      120                    125 | | 384 |
| tcg ccc aac ttc ggg gcc cac tgg atg aag gct ccc gtc tcc ttc agc<br>Ser Pro Asn Phe Gly Ala His Trp Met Lys Ala Pro Val Ser Phe Ser<br>    130                  135                    140 | | 432 |
| aaa gtc aag ctc acc aac aag ctc aac gga ggg ggc cag atc atg ctg<br>Lys Val Lys Leu Thr Asn Lys Leu Asn Gly Gly Gly Gln Ile Met Leu<br>145                    150                    155                  160 | | 480 |
| aac tcc ttg cat aag tat gag cct cga atc cac ata gtg aga gtt ggg<br>Asn Ser Leu His Lys Tyr Glu Pro Arg Ile His Ile Val Arg Val Gly<br>                165                    170                  175 | | 528 |
| gat cca cag cgc atg atc acc agc cac tgc ttc cct gag acc cag ttc<br>Asp Pro Gln Arg Met Ile Thr Ser His Cys Phe Pro Glu Thr Gln Phe<br>    180                  185                    190 | | 576 |
| ata gcg gtg act gct tat cag aac gag gag atc aca gct ctt aaa att<br>Ile Ala Val Thr Ala Tyr Gln Asn Glu Glu Ile Thr Ala Leu Lys Ile<br>                195                    200                  205 | | 624 |
| aag tac aat cca ttt gca aaa gct ttc ctt gat gca aag gaa aga agt<br>Lys Tyr Asn Pro Phe Ala Lys Ala Phe Leu Asp Ala Lys Glu Arg Ser<br>210                    215                    220 | | 672 |
| gat cac aaa gag atg atg gag gaa ccc gga gac agc cag caa cct ggg<br>Asp His Lys Glu Met Met Glu Glu Pro Gly Asp Ser Gln Gln Pro Gly<br>225                    230                    235                  240 | | 720 |
| tac tcc caa tgg ggg tgg ctt ctt cct gga acc agc acc ctg tgt cca<br>Tyr Ser Gln Trp Gly Trp Leu Leu Pro Gly Thr Ser Thr Leu Cys Pro<br>                245                    250                  255 | | 768 |
| cct gca aat cct cat cct cag ttt gga ggt gcc ctc tcc ctc ccc tcc<br>Pro Ala Asn Pro His Pro Gln Phe Gly Gly Ala Leu Ser Leu Pro Ser<br>                    260                    265                  270 | | 816 |
| acg cac agc tgt gac agg tac cca acc ctg agg agc cac cgg tcc tca<br>Thr His Ser Cys Asp Arg Tyr Pro Thr Leu Arg Ser His Arg Ser Ser<br>              275                    280                    285 | | 864 |
| ccc tac ccc agc ccc tat gct cat cgg aac aat tct cca acc tat tct<br>Pro Tyr Pro Ser Pro Tyr Ala His Arg Asn Asn Ser Pro Thr Tyr Ser<br>    290                  295                    300 | | 912 |
| gac aac tca cct gca tgt tta tcc atg ctg caa tcc cat gac aat tgg<br>Asp Asn Ser Pro Ala Cys Leu Ser Met Leu Gln Ser His Asp Asn Trp<br>305                    310                    315                  320 | | 960 |
| tcc agc ctt gga atg cct gcc cat ccc agc atg ctc ccc gtg agc cac<br>Ser Ser Leu Gly Met Pro Ala His Pro Ser Met Leu Pro Val Ser His<br>                325                    330                  335 | | 1008 |
| aat gcc agc cca cct acc agc tcc agt cag tac ccc agc ctg tgg tct<br>Asn Ala Ser Pro Pro Thr Ser Ser Ser Gln Tyr Pro Ser Leu Trp Ser<br>                    340                    345                  350 | | 1056 |
| gtg agc aac ggc gcc gtc acc ccg ggc tcc cag gca gca gcc gtg acc<br>Val Ser Asn Gly Ala Val Thr Pro Gly Ser Gln Ala Ala Ala Val Thr<br>              355                    360                    365 | | 1104 |
| aac ggg ctg ggg gcc cag ttc ttc cgg ggc tcc ccc gcg cac tac aca<br>Asn Gly Leu Gly Ala Gln Phe Phe Arg Gly Ser Pro Ala His Tyr Thr<br>    370                  375                    380 | | 1152 |
| ccc ctc acc cat ccg gtc tcg gca ccc tct tcc tcg gga tcc cca ctg<br>Pro Leu Thr His Pro Val Ser Ala Pro Ser Ser Ser Gly Ser Pro Leu<br>385                    390                    395                  400 | | 1200 |
| tac gaa ggg gcg gcc gcg gcc aca aac atc gtg gac agc cag tac gac<br>Tyr Glu Gly Ala Ala Ala Ala Thr Asn Ile Val Asp Ser Gln Tyr Asp<br>                    405                    410                  415 | | 1248 |
| gcc gca gcc caa ggc cgc ctc ata gcc tca tgg aca cct gtg tcg cca<br>Ala Ala Ala Gln Gly Arg Leu Ile Ala Ser Trp Thr Pro Val Ser Pro | | 1296 |

```
                    420             425             430
cct tcc atg                                                       1305
Pro Ser Met
        435

<210> SEQ ID NO 4
<211> LENGTH: 435
<212> TYPE: PRT
<213> ORGANISM: Homo sapiens

<400> SEQUENCE: 4

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Asp Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350
```

```
Val Ser Asn Gly Ala Val Thr Pro Gly Ser Gln Ala Ala Val Thr
        355                 360                 365
Asn Gly Leu Gly Ala Gln Phe Phe Arg Gly Ser Pro Ala His Tyr Thr
    370                 375                 380
Pro Leu Thr His Pro Val Ser Ala Pro Ser Ser Gly Ser Pro Leu
385                 390                 395                 400
Tyr Glu Gly Ala Ala Ala Ala Thr Asn Ile Val Asp Ser Gln Tyr Asp
                405                 410                 415
Ala Ala Ala Gln Gly Arg Leu Ile Ala Ser Trp Thr Pro Val Ser Pro
            420                 425                 430
Pro Ser Met
        435

<210> SEQ ID NO 5
<211> LENGTH: 9
<212> TYPE: PRT
<213> ORGANISM: Homo sapiens

<400> SEQUENCE: 5

Trp Leu Leu Pro Gly Thr Ser Thr Leu
1               5

<210> SEQ ID NO 6
<211> LENGTH: 9
<212> TYPE: PRT
<213> ORGANISM: Artificial
<220> FEATURE:
<223> OTHER INFORMATION: Agonist Peptide

<400> SEQUENCE: 6

Trp Leu Leu Pro Gly Thr Ser Thr Val
1               5

<210> SEQ ID NO 7
<211> LENGTH: 9
<212> TYPE: PRT
<213> ORGANISM: Homo sapiens

<400> SEQUENCE: 7

Ser Gln Tyr Pro Ser Leu Trp Ser Val
1               5

<210> SEQ ID NO 8
<211> LENGTH: 9
<212> TYPE: PRT
<213> ORGANISM: Homo sapiens

<400> SEQUENCE: 8

Arg Leu Ile Ala Ser Trp Thr Pro Val
1               5

<210> SEQ ID NO 9
<211> LENGTH: 10
<212> TYPE: PRT
<213> ORGANISM: Homo sapiens

<400> SEQUENCE: 9

Ala Met Tyr Ser Phe Leu Leu Asp Phe Val
1               5                   10

<210> SEQ ID NO 10
<211> LENGTH: 410
```

```
<212> TYPE: PRT
<213> ORGANISM: Artificial
<220> FEATURE:
<223> OTHER INFORMATION: Synthetic Construct

<400> SEQUENCE: 10

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Asp Pro Gln Arg Met Ile Thr Ser His Cys Phe Pro Glu Thr Gln Phe
            180                 185                 190

Ile Ala Val Thr Ala Arg Ser Asp His Lys Glu Met Met Glu Glu Pro
        195                 200                 205

Gly Asp Ser Gln Gln Pro Gly Tyr Ser Gln Trp Gly Trp Leu Leu Pro
    210                 215                 220

Gly Thr Ser Thr Leu Cys Pro Ala Asn Pro His Pro Gln Phe Gly
225                 230                 235                 240

Gly Ala Leu Ser Leu Pro Ser Thr His Ser Cys Asp Arg Tyr Pro Thr
                245                 250                 255

Leu Arg Ser His Arg Ser Ser Pro Tyr Pro Ser Pro Tyr Ala His Arg
            260                 265                 270

Asn Asn Ser Pro Thr Tyr Ser Asp Asn Ser Pro Ala Cys Leu Ser Met
        275                 280                 285

Leu Gln Ser His Asp Asn Trp Ser Ser Leu Gly Met Pro Ala His Pro
    290                 295                 300

Ser Met Leu Pro Val Ser His Asn Ala Ser Pro Pro Thr Ser Ser Ser
305                 310                 315                 320

Gln Tyr Pro Ser Leu Trp Ser Val Ser Asn Gly Ala Val Thr Pro Gly
                325                 330                 335

Ser Gln Ala Ala Ala Val Thr Asn Gly Leu Gly Ala Gln Phe Phe Arg
            340                 345                 350

Gly Ser Pro Ala His Tyr Thr Pro Leu Thr His Pro Val Ser Ala Pro
        355                 360                 365

Ser Ser Ser Gly Ser Pro Leu Tyr Glu Gly Ala Ala Ala Ala Thr Asn
    370                 375                 380
```

```
Ile Val Asp Ser Gln Tyr Asp Ala Ala Ala Gln Gly Arg Leu Ile Ala
385                 390                 395                 400

Ser Trp Thr Pro Val Ser Pro Pro Ser Met
                405                 410

<210> SEQ ID NO 11
<211> LENGTH: 1295
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1275)

<400> SEQUENCE: 11 gaattccgc atg gcc gat gaa gct ccg agc tcc cct ggc acc gag agc gcg      51
          Met Ala Asp Glu Ala Pro Ser Ser Pro Gly Thr Glu Ser Ala
           1               5                  10 gga aag agc ctg cag tac cga gtg gac cac ctg ctg agc gcc gtg gag       99
Gly Lys Ser Leu Gln Tyr Arg Val Asp His Leu Leu Ser Ala Val Glu
 15                  20                  25                  30 aat gag ctg cag gcg ggc agc gag aag ggc gac ccc aca gag cgc gaa      147
Asn Glu Leu Gln Ala Gly Ser Glu Lys Gly Asp Pro Thr Glu Arg Glu
                 35                  40                  45 ctg cgc gtg ggc ctg gag gag agc gag ctg tgg ctg cgc ttc aag gag      195
Leu Arg Val Gly Leu Glu Glu Ser Glu Leu Trp Leu Arg Phe Lys Glu
             50                  55                  60 ctc acc aat gag atg atc gtg acc aag aac ggc agg agg atg ttt ccg      243
Leu Thr Asn Glu Met Ile Val Thr Lys Asn Gly Arg Arg Met Phe Pro
 65                  70                  75 gtg ctg aag gtg aac gtg tct ggc ctg gac ccc aac gcc atg tac tcc      291
Val Leu Lys Val Asn Val Ser Gly Leu Asp Pro Asn Ala Met Tyr Ser
 80                  85                  90 ttc ctg ctg gac ttc gtg gcg gcg gac aac cac cgc tgg aag tac gtg      339
Phe Leu Leu Asp Phe Val Ala Ala Asp Asn His Arg Trp Lys Tyr Val
 95                 100                 105                 110 aac ggg gaa tgg gtg ccg ggg ggc aag ccg gag ccg cag gcg ccc agc      387
Asn Gly Glu Trp Val Pro Gly Gly Lys Pro Glu Pro Gln Ala Pro Ser
                115                 120                 125 tgc gtc tac atc cac ccc gac tcg ccc aac ttc ggg gcc cac tgg atg      435
Cys Val Tyr Ile His Pro Asp Ser Pro Asn Phe Gly Ala His Trp Met
            130                 135                 140 aag gct ccc gtc tcc ttc agc aaa gtc aag ctc acc aac aag ctc aac      483
Lys Ala Pro Val Ser Phe Ser Lys Val Lys Leu Thr Asn Lys Leu Asn
        145                 150                 155 gga ggg ggc cag atc atg ctg aac tcc ttg cat aag tat gag cct cga      531
Gly Gly Gly Gln Ile Met Leu Asn Ser Leu His Lys Tyr Glu Pro Arg
160                 165                 170 atc cac ata gtg aga gtt ggg gat cca cag cgc atg atc acc agc cac      579
Ile His Ile Val Arg Val Gly Asp Pro Gln Arg Met Ile Thr Ser His
175                 180                 185                 190 tgc ttc cct gag acc cag ttc ata gcg gtg act gct aga agt gat cac      627
Cys Phe Pro Glu Thr Gln Phe Ile Ala Val Thr Ala Arg Ser Asp His
                195                 200                 205 aaa gag atg atg gag gaa ccc gga gac agc cag caa cct ggg tac tcc      675
Lys Glu Met Met Glu Glu Pro Gly Asp Ser Gln Gln Pro Gly Tyr Ser
            210                 215                 220 caa tgg ggg tgg ctt ctt cct gga acc agc acc ctg tgt cca cct gca      723
Gln Trp Gly Trp Leu Leu Pro Gly Thr Ser Thr Leu Cys Pro Pro Ala
        225                 230                 235
```

| | | |
|---|---|---|
| aat cct cat cct cag ttt gga ggt gcc ctc tcc ctc ccc tcc acg cac<br>Asn Pro His Pro Gln Phe Gly Gly Ala Leu Ser Leu Pro Ser Thr His<br>240                         245                              250 | | 771 |
| agc tgt gac agg tac cca acc ctg agg agc cac cgg tcc tca ccc tac<br>Ser Cys Asp Arg Tyr Pro Thr Leu Arg Ser His Arg Ser Ser Pro Tyr<br>255                         260                     265                     270 | | 819 |
| ccc agc ccc tat gct cat cgg aac aat tct cca acc tat tct gac aac<br>Pro Ser Pro Tyr Ala His Arg Asn Asn Ser Pro Thr Tyr Ser Asp Asn<br>275                         280                            285 | | 867 |
| tca cct gca tgt tta tcc atg ctg caa tcc cat gac aat tgg tcc agc<br>Ser Pro Ala Cys Leu Ser Met Leu Gln Ser His Asp Asn Trp Ser Ser<br>               290                     295                     300 | | 915 |
| ctt gga atg cct gcc cat ccc agc atg ctc ccc gtg agc cac aat gcc<br>Leu Gly Met Pro Ala His Pro Ser Met Leu Pro Val Ser His Asn Ala<br>305                         310                     315 | | 963 |
| agc cca cct acc agc tcc agt cag tac ccc agc ctg tgg tct gtg agc<br>Ser Pro Pro Thr Ser Ser Ser Gln Tyr Pro Ser Leu Trp Ser Val Ser<br>        320                     325                     330 | | 1011 |
| aac ggc gcc gtc acc ccg ggc tcc cag gca gca gcc gtg acc aac ggg<br>Asn Gly Ala Val Thr Pro Gly Ser Gln Ala Ala Ala Val Thr Asn Gly<br>335                         340                     345                     350 | | 1059 |
| ctg ggg gcc cag ttc ttc cgg ggc tcc ccc gcg cac tac aca ccc ctc<br>Leu Gly Ala Gln Phe Phe Arg Gly Ser Pro Ala His Tyr Thr Pro Leu<br>               355                     360                     365 | | 1107 |
| acc cat ccg gtc tcg gca ccc tct tcc tcg gga tcc cca ctg tac gaa<br>Thr His Pro Val Ser Ala Pro Ser Ser Ser Gly Ser Pro Leu Tyr Glu<br>370                         375                     380 | | 1155 |
| ggg gcg gcc gcg gcc aca aac atc gtg gac agc cag tac gac gcc gca<br>Gly Ala Ala Ala Ala Thr Asn Ile Val Asp Ser Gln Tyr Asp Ala Ala<br>385                         390                     395 | | 1203 |
| gcc caa ggc cgc ctc ata gcc tca tgg aca cct gtg tcg cca cct tcc<br>Ala Gln Gly Arg Leu Ile Ala Ser Trp Thr Pro Val Ser Pro Pro Ser<br>        400                     405                     410 | | 1251 |
| atg cat cac cat cac cat cac tga gactagtccc gggcggccgc<br>Met His His His His His His<br>415                         420 | | 1295 |

<210> SEQ ID NO 12
<211> LENGTH: 421
<212> TYPE: PRT
<213> ORGANISM: Artificial
<220> FEATURE:
<223> OTHER INFORMATION: Synthetic Construct

<400> SEQUENCE: 12

Met Ala Asp Glu Ala Pro Ser Ser Pro Gly Thr Glu Ser Ala Gly Lys
1                 5                    10                   15

Ser Leu Gln Tyr Arg Val Asp His Leu Leu Ser Ala Val Glu Asn Glu
                20                    25                    30

Leu Gln Ala Gly Ser Glu Lys Gly Asp Pro Thr Glu Arg Glu Leu Arg
         35                    40                    45

Val Gly Leu Glu Glu Ser Glu Leu Trp Leu Arg Phe Lys Glu Leu Thr
     50                     55                    60

Asn Glu Met Ile Val Thr Lys Asn Gly Arg Arg Met Phe Pro Val Leu
65                 70                    75                   80

Lys Val Asn Val Ser Gly Leu Asp Pro Asn Ala Met Tyr Ser Phe Leu
                85                    90                    95

Leu Asp Phe Val Ala Ala Asp Asn His Arg Trp Lys Tyr Val Asn Gly
         100                    105                   110

Glu Trp Val Pro Gly Gly Lys Pro Glu Pro Gln Ala Pro Ser Cys Val
            115                 120                 125

Tyr Ile His Pro Asp Ser Pro Asn Phe Gly Ala His Trp Met Lys Ala
130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175

Ile Val Arg Val Gly Asp Pro Gln Arg Met Ile Thr Ser His Cys Phe
            180                 185                 190

Pro Glu Thr Gln Phe Ile Ala Val Thr Ala Arg Ser Asp His Lys Glu
    195                 200                 205

Met Met Glu Glu Pro Gly Asp Ser Gln Gln Pro Gly Tyr Ser Gln Trp
210                 215                 220

Gly Trp Leu Leu Pro Gly Thr Ser Thr Leu Cys Pro Pro Ala Asn Pro
225                 230                 235                 240

His Pro Gln Phe Gly Gly Ala Leu Ser Leu Pro Ser Thr His Ser Cys
                245                 250                 255

Asp Arg Tyr Pro Thr Leu Arg Ser His Arg Ser Ser Pro Tyr Pro Ser
            260                 265                 270

Pro Tyr Ala His Arg Asn Asn Ser Pro Thr Tyr Ser Asp Asn Ser Pro
    275                 280                 285

Ala Cys Leu Ser Met Leu Gln Ser His Asp Asn Trp Ser Ser Leu Gly
290                 295                 300

Met Pro Ala His Pro Ser Met Leu Pro Val Ser His Asn Ala Ser Pro
305                 310                 315                 320

Pro Thr Ser Ser Ser Gln Tyr Pro Ser Leu Trp Ser Val Ser Asn Gly
                325                 330                 335

Ala Val Thr Pro Gly Ser Gln Ala Ala Ala Val Thr Asn Gly Leu Gly
            340                 345                 350

Ala Gln Phe Phe Arg Gly Ser Pro Ala His Tyr Thr Pro Leu Thr His
    355                 360                 365

Pro Val Ser Ala Pro Ser Ser Ser Gly Ser Pro Leu Tyr Glu Gly Ala
370                 375                 380

Ala Ala Ala Thr Asn Ile Val Asp Ser Gln Tyr Asp Ala Ala Ala Gln
385                 390                 395                 400

Gly Arg Leu Ile Ala Ser Trp Thr Pro Val Ser Pro Pro Ser Met His
                405                 410                 415

His His His His
        420

<210> SEQ ID NO 13
<211> LENGTH: 410
<212> TYPE: PRT
<213> ORGANISM: Artificial
<220> FEATURE:
<223> OTHER INFORMATION: Synthetic Construct

<400> SEQUENCE: 13

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

```
Ser Glu Leu Trp Leu Arg Phe Lys Glu Leu Thr Asn Glu Met Ile Val
 50                  55                  60

Thr Lys Asn Gly Arg Arg Met Phe Pro Val Leu Lys Val Asn Val Ser
 65                  70                  75                  80

Gly Leu Asp Pro Asn Ala Met Tyr Ser Phe Leu Leu Asp Phe Val Ala
                 85                  90                  95

Ala Asp Asn His Arg Trp Lys Tyr Val Asn Gly Trp Val Pro Gly
            100                 105                 110

Gly Lys Pro Glu Pro Gln Ala Pro Ser Cys Val Tyr Ile His Pro Asp
            115                 120                 125

Ser Pro Asn Phe Gly Ala His Trp Met Lys Ala Pro Val Ser Phe Ser
130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Asp Pro Gln Arg Met Ile Thr Ser His Cys Phe Pro Glu Thr Gln Phe
            180                 185                 190

Ile Ala Val Thr Ala Arg Ser Asp His Lys Glu Met Met Glu Glu Pro
            195                 200                 205

Gly Asp Ser Gln Gln Pro Gly Tyr Ser Gln Trp Gly Trp Leu Leu Pro
210                 215                 220

Gly Thr Ser Thr Val Cys Pro Pro Ala Asn Pro His Pro Gln Phe Gly
225                 230                 235                 240

Gly Ala Leu Ser Leu Pro Ser Thr His Ser Cys Asp Arg Tyr Pro Thr
                245                 250                 255

Leu Arg Ser His Arg Ser Ser Pro Tyr Pro Ser Pro Tyr Ala His Arg
            260                 265                 270

Asn Asn Ser Pro Thr Tyr Ser Asp Asn Ser Pro Ala Cys Leu Ser Met
            275                 280                 285

Leu Gln Ser His Asp Asn Trp Ser Ser Leu Gly Met Pro Ala His Pro
290                 295                 300

Ser Met Leu Pro Val Ser His Asn Ala Ser Pro Pro Thr Ser Ser Ser
305                 310                 315                 320

Gln Tyr Pro Ser Leu Trp Ser Val Ser Asn Gly Ala Val Thr Pro Gly
                325                 330                 335

Ser Gln Ala Ala Ala Val Thr Asn Gly Leu Gly Ala Gln Phe Phe Arg
            340                 345                 350

Gly Ser Pro Ala His Tyr Thr Pro Leu Thr His Pro Val Ser Ala Pro
            355                 360                 365

Ser Ser Ser Gly Ser Pro Leu Tyr Glu Gly Ala Ala Ala Thr Asn
370                 375                 380

Ile Val Asp Ser Gln Tyr Asp Ala Ala Gln Gly Arg Leu Ile Ala
385                 390                 395                 400

Ser Trp Thr Pro Val Ser Pro Pro Ser Met
                405                 410

<210> SEQ ID NO 14
<211> LENGTH: 1295
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (10)..(1275)
```

<400> SEQUENCE: 14

```
gaattccgc atg gcc gat gaa gct ccg agc tcc cct ggc acc gag agc gcg      51
          Met Ala Asp Glu Ala Pro Ser Ser Pro Gly Thr Glu Ser Ala
          1               5                   10 gga aag agc ctg cag tac cga gtg gac cac ctg ctg agc gcc gtg gag        99
Gly Lys Ser Leu Gln Tyr Arg Val Asp His Leu Leu Ser Ala Val Glu
15                  20                  25                  30 aat gag ctg cag gcg ggc agc gag aag ggc gac ccc aca gag cgc gaa       147
Asn Glu Leu Gln Ala Gly Ser Glu Lys Gly Asp Pro Thr Glu Arg Glu
                35                  40                  45 ctg cgc gtg ggc ctg gag gag agc gag ctg tgg ctg cgc ttc aag gag       195
Leu Arg Val Gly Leu Glu Glu Ser Glu Leu Trp Leu Arg Phe Lys Glu
            50                  55                  60 ctc acc aat gag atg atc gtg acc aag aac ggc agg agg atg ttt ccg       243
Leu Thr Asn Glu Met Ile Val Thr Lys Asn Gly Arg Arg Met Phe Pro
        65                  70                  75 gtg ctg aag gtg aac gtg tct ggc ctg gac ccc aac gcc atg tac tcc       291
Val Leu Lys Val Asn Val Ser Gly Leu Asp Pro Asn Ala Met Tyr Ser
    80                  85                  90 ttc ctg ctg gac ttc gtg gcg gcg gac aac cac cgc tgg aag tac gtg       339
Phe Leu Leu Asp Phe Val Ala Ala Asp Asn His Arg Trp Lys Tyr Val
95                  100                 105                 110 aac ggg gaa tgg gtg ccg ggg ggc aag ccg gag ccg cag gcg ccc agc       387
Asn Gly Glu Trp Val Pro Gly Gly Lys Pro Glu Pro Gln Ala Pro Ser
                115                 120                 125 tgc gtc tac atc cac ccc gac tcg ccc aac ttc ggg gcc cac tgg atg       435
Cys Val Tyr Ile His Pro Asp Ser Pro Asn Phe Gly Ala His Trp Met
            130                 135                 140 aag gct ccc gtc tcc ttc agc aaa gtc aag ctc acc aac aag ctc aac       483
Lys Ala Pro Val Ser Phe Ser Lys Val Lys Leu Thr Asn Lys Leu Asn
        145                 150                 155 gga ggg ggc cag atc atg ctg aac tcc ttg cat aag tat gag cct cga       531
Gly Gly Gly Gln Ile Met Leu Asn Ser Leu His Lys Tyr Glu Pro Arg
    160                 165                 170 atc cac ata gtg aga gtt ggg gat cca cag cgc atg atc acc agc cac       579
Ile His Ile Val Arg Val Gly Asp Pro Gln Arg Met Ile Thr Ser His
175                 180                 185                 190 tgc ttc cct gag acc cag ttc ata gcg gtg act gct aga agt gat cac       627
Cys Phe Pro Glu Thr Gln Phe Ile Ala Val Thr Ala Arg Ser Asp His
                195                 200                 205 aaa gag atg atg gag gaa ccc gga gac agc cag caa cct ggg tac tcc       675
Lys Glu Met Met Glu Glu Pro Gly Asp Ser Gln Gln Pro Gly Tyr Ser
            210                 215                 220 caa tgg ggg tgg ctt ctt cct gga acc agc acc gtg tgt cca cct gca       723
Gln Trp Gly Trp Leu Leu Pro Gly Thr Ser Thr Val Cys Pro Pro Ala
        225                 230                 235 aat cct cat cct cag ttt gga ggt gcc ctc tcc ctc ccc tcc acg cac       771
Asn Pro His Pro Gln Phe Gly Gly Ala Leu Ser Leu Pro Ser Thr His
    240                 245                 250 agc tgt gac agg tac cca acc ctg agg agc cac cgg tcc tca ccc tac       819
Ser Cys Asp Arg Tyr Pro Thr Leu Arg Ser His Arg Ser Ser Pro Tyr
255                 260                 265                 270 ccc agc ccc tat gct cat cgg aac aat tct cca acc tat tct gac aac       867
Pro Ser Pro Tyr Ala His Arg Asn Asn Ser Pro Thr Tyr Ser Asp Asn
                275                 280                 285 tca cct gca tgt tta tcc atg ctg caa tcc cat gac aat tgg tcc agc       915
Ser Pro Ala Cys Leu Ser Met Leu Gln Ser His Asp Asn Trp Ser Ser
            290                 295                 300
```

```
ctt gga atg cct gcc cat ccc agc atg ctc ccc gtg agc cac aat gcc     963
Leu Gly Met Pro Ala His Pro Ser Met Leu Pro Val Ser His Asn Ala
        305                 310                 315 agc cca cct acc agc tcc agt cag tac ccc agc ctg tgg tct gtg agc    1011
Ser Pro Pro Thr Ser Ser Ser Gln Tyr Pro Ser Leu Trp Ser Val Ser
320                 325                 330 aac ggc gcc gtc acc ccg ggc tcc cag gca gca gcc gtg acc aac ggg    1059
Asn Gly Ala Val Thr Pro Gly Ser Gln Ala Ala Ala Val Thr Asn Gly
335                 340                 345                 350 ctg ggg gcc cag ttc ttc cgg ggc tcc ccc gcg cac tac aca ccc ctc    1107
Leu Gly Ala Gln Phe Phe Arg Gly Ser Pro Ala His Tyr Thr Pro Leu
                355                 360                 365 acc cat ccg gtc tcg gca ccc tct tcc tcg gga tcc cca ctg tac gaa    1155
Thr His Pro Val Ser Ala Pro Ser Ser Ser Gly Ser Pro Leu Tyr Glu
                370                 375                 380 ggg gcg gcc gcg gcc aca aac atc gtg gac agc cag tac gac gcc gca    1203
Gly Ala Ala Ala Ala Thr Asn Ile Val Asp Ser Gln Tyr Asp Ala Ala
                    385                 390                 395 gcc caa ggc cgc ctc ata gcc tca tgg aca cct gtg tcg cca cct tcc    1251
Ala Gln Gly Arg Leu Ile Ala Ser Trp Thr Pro Val Ser Pro Pro Ser
    400                 405                 410 atg cat cac cat cac cat cac tga gactagtccc gggcggccgc              1295
Met His His His His His His
415                 420

<210> SEQ ID NO 15
<211> LENGTH: 421
<212> TYPE: PRT
<213> ORGANISM: Artificial
<220> FEATURE:
<223> OTHER INFORMATION: Synthetic Construct

<400> SEQUENCE: 15

Met Ala Asp Glu Ala Pro Ser Ser Pro Gly Thr Glu Ser Ala Gly Lys
1               5                   10                  15

Ser Leu Gln Tyr Arg Val Asp His Leu Leu Ser Ala Val Glu Asn Glu
            20                  25                  30

Leu Gln Ala Gly Ser Glu Lys Gly Asp Pro Thr Glu Arg Glu Leu Arg
        35                  40                  45

Val Gly Leu Glu Glu Ser Glu Leu Trp Leu Arg Phe Lys Glu Leu Thr
    50                  55                  60

Asn Glu Met Ile Val Thr Lys Asn Gly Arg Arg Met Phe Pro Val Leu
65                  70                  75                  80

Lys Val Asn Val Ser Gly Leu Asp Pro Asn Ala Met Tyr Ser Phe Leu
                85                  90                  95

Leu Asp Phe Val Ala Ala Asp Asn His Arg Trp Lys Tyr Val Asn Gly
            100                 105                 110

Glu Trp Val Pro Gly Gly Lys Pro Glu Pro Gln Ala Pro Ser Cys Val
        115                 120                 125

Tyr Ile His Pro Asp Ser Pro Asn Phe Gly Ala His Trp Met Lys Ala
    130                 135                 140

Pro Val Ser Phe Ser Lys Val Lys Leu Thr Asn Lys Leu Asn Gly Gly
145                 150                 155                 160

Gly Gln Ile Met Leu Asn Ser Leu His Lys Tyr Glu Pro Arg Ile His
                165                 170                 175
```

```
Ile Val Arg Val Gly Asp Pro Gln Arg Met Ile Thr Ser His Cys Phe
            180                 185                 190

Pro Glu Thr Gln Phe Ile Ala Val Thr Ala Arg Ser Asp His Lys Glu
        195                 200                 205

Met Met Glu Glu Pro Gly Asp Ser Gln Gln Pro Gly Tyr Ser Gln Trp
    210                 215                 220

Gly Trp Leu Leu Pro Gly Thr Ser Thr Val Cys Pro Pro Ala Asn Pro
225                 230                 235                 240

His Pro Gln Phe Gly Gly Ala Leu Ser Leu Pro Ser Thr His Ser Cys
            245                 250                 255

Asp Arg Tyr Pro Thr Leu Arg Ser His Arg Ser Ser Pro Tyr Pro Ser
            260                 265                 270

Pro Tyr Ala His Arg Asn Asn Ser Pro Thr Tyr Ser Asp Asn Ser Pro
        275                 280                 285

Ala Cys Leu Ser Met Leu Gln Ser His Asp Asn Trp Ser Ser Leu Gly
        290                 295                 300

Met Pro Ala His Pro Ser Met Leu Pro Val Ser His Asn Ala Ser Pro
305                 310                 315                 320

Pro Thr Ser Ser Ser Gln Tyr Pro Ser Leu Trp Ser Val Ser Asn Gly
                325                 330                 335

Ala Val Thr Pro Gly Ser Gln Ala Ala Ala Val Thr Asn Gly Leu Gly
            340                 345                 350

Ala Gln Phe Phe Arg Gly Ser Pro Ala His Tyr Thr Pro Leu Thr His
            355                 360                 365

Pro Val Ser Ala Pro Ser Ser Ser Gly Ser Pro Leu Tyr Glu Gly Ala
        370                 375                 380

Ala Ala Ala Thr Asn Ile Val Asp Ser Gln Tyr Asp Ala Ala Ala Gln
385                 390                 395                 400

Gly Arg Leu Ile Ala Ser Trp Thr Pro Val Ser Pro Pro Ser Met His
                405                 410                 415

His His His His His
            420

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 16

Met Ala Asp Glu Ala Pro
1               5
```

MODIFIED YEAST-BRACHYURY IMMUNOTHERAPEUTIC COMPOSITIONS

CROSS-REFERENCE TO RELATED APPLICATIONS

This application is a national stage application under 35 U.S.C. 371 of PCT Application No. PCT/US2016/044977, having an international filing date of Aug. 1, 2016, which designated the United States, which PCT application claimed the benefit of U.S. Provisional Application Ser. No. 62/200,497, filed Aug. 3, 2015, both of which are incorporated herein by reference in their entirety.

GOVERNMENT RIGHTS

This invention was created in the performance of a Cooperative Research and Development Agreement with the National Institutes of Health, an Agency of the Department of Health and Human Services. The Government of the United States has certain rights in this invention.

STATEMENT REGARDING JOINT RESEARCH AGREEMENT

This invention was made by or on behalf of parties to a Cooperative Research and Development Agreement, executed May 8, 2008. The parties to the Cooperative Research and Development Agreement are: GlobeImmune, Inc. and the U.S. Department of Health and Human Services, as represented by National Cancer Institute, an Institute, Center or Division of the National Institutes of Health.

REFERENCE TO A SEQUENCE LISTING

This application contains a Sequence Listing submitted electronically as a text file by EFS-Web. The text file, named "7797-3-PCT_ST25", has a size in bytes of 50 KB, and was recorded on Jul. 26, 2016. The information contained in the text file is incorporated herein by reference in its entirety pursuant to 37 CFR § 1.52(e)(5).

FIELD OF THE INVENTION

The present invention generally relates to improved yeast-Brachyury immunotherapeutic compositions and methods for the prevention and/or treatment of cancers characterized by the expression or overexpression of Brachyury as well as methods to improve the manufacture and use of yeast-Brachyury immunotherapeutic compositions.

BACKGROUND OF THE INVENTION

Brachyury, also known as "T", is a mesodermal transcription factor and member of the T-box complex of genes. The gene encoding Brachyury (denoted as either T gene or Brachyury gene in humans) was initially identified in 1927 by Nadine Dobrovolskaïa-Zavadskaïa through a mutation in mice that affected tail length and sacral vertebrae in heterozygous animals. The Brachyury gene was cloned in mice in 1990 by Hermann and colleagues (Herrmann et al., 1990, *Nature* 343:617-622) and in humans in 1996 by Edwards and colleagues (Edwards et al., 1996, *Genome Res.* 6:226-223), who also described the deduced amino acid sequence for human Brachyury.

As a member of the T-box family of transcription factors, Brachyury contains the highly conserved DNA-binding domain motif, called "T-box" or T-domain, which binds to a palindromic consensus sequence. Brachyury, like other T-box proteins, has been shown to play a role in early development, and is vital for the formation and differentiation of posterior mesoderm and axial development in vertebrates (see, e.g., Wilkinson et al., 1990, *Nature* 343(6259): 657-659); Beddington et al., 1992, *Development* (Suppl.): 157-165; Schulte-Merker et al., 1994, *Development* 120: 1009-1015; Kispert and Herrmann, 1994, *Dev. Biol.* 161: 179-193; Showell et al., 2004, *Dev Dyn* 229:201-218). More recently, Palena and colleagues have demonstrated that Brachyury is expressed in a variety of human tumor tissues and cancer cell lines and have shown that peptides of Brachyury can be used to generate Brachyury-specific T cell lines in normal donors and cancer patients (Palena et al., 2007, *Clin. Cancer Res.* 13(8):2471-2478). Studies by Fernando et al. have shown that Brachyury promotes the epithelial-mesenchymal transition (EMT) in human tumor cells, conferring on tumor cells a mesenchymal phenotype, as well as migratory and invasive abilities, while attenuating tumor cell cycle progression (Fernando et al., 2010, *J. Clin. Invest.* 120(2):533-544). Accordingly, Brachyury is involved in metastatic progression of cancer.

Cancer is a leading cause of death worldwide, and the development of effective therapies for cancer continues to be one of the most active areas of research and clinical development. Although a variety of innovative approaches to treat and prevent cancers have been proposed, many cancers continue to have a high rate of mortality and may be difficult to treat or relatively unresponsive to conventional therapies. Cancers associated with Brachyury expression may be found in a variety of tissues, including breast, small intestine, stomach, kidney, bladder, uterus, ovary, testes, lung, colon, bone (including chordomas) and prostate, and includes metastatic and late-stage cancers. In addition, Brachyury is expressed in tumors of B cell origin, such as chronic lymphocytic leukemia (CLL), Epstein-Barr virus transformed B cells, Burkitt's and Hodgkin's lymphomas. Therefore, Brachyury appears to play a role in a large number of human cancers. While Brachyury has been proposed to be a target for cancer immunotherapy (see, e.g., Palena et al., supra, Fernando et al., supra, and WO 2008/106551), since this is a relatively new cancer target, there remains a need in the art for new immunotherapeutic products that effectively treat and/or prevent cancers associated with Brachyury expression or overexpression.

SUMMARY OF THE INVENTION

One embodiment of the invention relates to a yeast-Brachyury immunotherapeutic composition comprising: a) a yeast; and b) at least one modified Brachyury antigen expressed by the yeast, wherein the modified Brachyury antigen has an amino acid sequence that differs from a wild-type Brachyury amino acid sequence by at least one modification selected from a deletion or substitution of an amino acid at any one or more of positions 42 through 229 of the wild-type Brachyury, wherein the Brachyury antigen has a disrupted DNA binding site as compared to the wild-type Brachyury. In one aspect, the modified Brachyury antigen has disrupted DNA binding activity as compared to the wild-type Brachyury. In still another aspect, the yeast have a reduced flocculation phenotype as compared to a yeast expressing a wild-type Brachyury. In one aspect, the modified Brachyury antigen has an amino acid sequence that differs from a wild-type Brachyury amino acid sequence by at least one modification selected from a deletion or substitution of an amino acid at any one or more of positions 66 to 217 of the wild-type Brachyury. In one aspect, the modified Brachyury antigen has an amino acid sequence that differs from a wild-type Brachyury amino acid sequence by at least one modification selected from a deletion or substitution of an amino acid at any one or more of positions 198 to 222 of the wild-type Brachyury. In one aspect, the modified Brachyury antigen has an amino acid sequence that differs from a wild-type Brachyury amino acid sequence by at least one modification selected from a deletion or substitution of at least 1, 2, 3, 4, 5, 6, 7, 8, 9, 10, 11, 12, 13, 14, 15, 16, 17, 18, 19 or 20 amino acid residues of the wild-type Brachyury selected from: Lys66, Arg69, Arg70, Arg101, Lys103, Lys147, Asn150, Lys151, Ser162, Thr196, Ala197, Tyr198, Ile208, Asn211, Pro212, Phe213, Ala214, Lys215, Ala216, and/or Phe217. In one aspect, the modified Brachyury antigen has an amino acid sequence that differs from a wild-type Brachyury amino acid sequence by at least one modification selected from a deletion or substitution of at least 1, 2, 3, 4, 5, 6, 7, or 8 amino acid residues of the wild-type Brachyury selected from: Met87, Pro127, Asp128, Ser129, Pro130, Asn131, Phe132, and/or Val175. In still another aspect, the modification is a deletion. In yet another aspect, the modified Brachyury antigen differs from a wild-type Brachyury amino acid sequence by 1, 2, 3, 4, 5, 6, 7, 8, 9, 10, 11, 12, 13, 14, 15, 16, 17, 18. 19, 20, 21, 22, 23, or 24 of the modifications. In still another aspect, the modified Brachyury antigen has an amino acid sequence that differs from a wild-type Brachyury amino acid sequence by a deletion of at least 1, 2, 3, 4, 5, 6, 7, 8, 9, 10, 11, 12, 13, 14, 15, 16, 17, 18, 19, 20, 21, 22, 23, or 24 contiguous amino acids between positions 66 and 217 of the wild-type Brachyury. In one aspect, the modified Brachyury antigen has an amino acid sequence that differs from a wild-type Brachyury amino acid sequence by a deletion of at least 1, 2, 3, 4, 5, 6, 7, 8, 9, 10, 11, 12, 13, 14, 15, 16, 17, 18, 19, 20, 21, 22, 23, or 24 contiguous amino acids between positions 198 and 222 of the wild-type Brachyury. In one aspect, the modified Brachyury antigen has an amino acid sequence that differs from a wild-type Brachyury amino acid sequence by a deletion of positions 198-222 of the wild-type Brachyury.

In one aspect of any of the embodiments or aspects of the invention described above or elsewhere herein, the modified Brachyury antigen has an amino acid sequence further comprising at least one agonist T cell epitope. In one aspect, the agonist epitope has the amino acid sequence of SEQ ID NO:6.

In one aspect of any of the embodiments or aspects of the invention described above or elsewhere herein, the modified Brachyury antigen has an amino acid sequence that is at least 80% identical to SEQ ID NO:10 or SEQ ID NO:13. In one aspect, the modified Brachyury antigen has an amino acid sequence that is at least 90% identical to SEQ ID NO:10 or SEQ ID NO:13. In one aspect, the modified Brachyury antigen has an amino acid sequence that is at least 95% identical to SEQ ID NO:10 or SEQ ID NO:13. In still another aspect, the modified Brachyury antigen has an amino acid sequence comprising SEQ ID NO:10 or positions 2-410 of SEQ ID NO:10. In one aspect, the modified Brachyury antigen has an amino acid sequence comprising SEQ ID NO:13 or positions 2-410 of SEQ ID NO:13. In one aspect, the modified Brachyury antigen is a fusion protein having an amino acid sequence that is at least 95% identical to SEQ ID NO:12 or SEQ ID NO:15. In one aspect, the modified Brachyury antigen is a fusion protein having an amino acid sequence of SEQ ID NO:12 or SEQ ID NO:15.

In any of the foregoing aspects of any of the embodiments of the invention described above or elsewhere herein, the yeast is from *Saccharomyces*. In one aspect, the yeast is from *Saccharomyces cerevisiae*. In one aspect, the yeast is a whole yeast. In one aspect, the whole yeast is killed. In one aspect, the whole yeast is heat-inactivated.

In one aspect of any of the embodiments of the invention described above or elsewhere herein, the composition is formulated in a pharmaceutically acceptable excipient suitable for administration to a subject.

Yet another embodiment of the invention relates to a yeast-Brachyury immunotherapeutic composition comprising: a) a whole, inactivated yeast; and b) a Brachyury fusion protein comprising the amino acid sequence of positions 2-415 of SEQ ID NO:10, wherein the Brachyury fusion protein was expressed by the yeast; and wherein the composition elicits a Brachyury-specific T cell response. In one aspect, the fusion protein has an amino acid sequence of SEQ ID NO:12. Still another embodiment of the invention relates to a yeast-Brachyury immunotherapeutic composition comprising: a) a whole, inactivated yeast; and a Brachyury fusion protein comprising the amino acid sequence of positions 2-415 of SEQ ID NO:13; wherein the Brachyury fusion protein was expressed by the yeast; and wherein the composition elicits a Brachyury-specific T cell response. In one aspect, the fusion protein has an amino acid sequence of SEQ ID NO:15.

In any of the embodiments or aspects of the invention described above or elsewhere herein, expression of the Brachyury fusion protein is under the control of the promoter CUP1. In one aspect, the yeast is from *Saccharomyces*. In one aspect, the yeast is from *Saccharomyces cerevisiae*. In one aspect, the composition is formulated in a pharmaceutically acceptable excipient suitable for administration to a subject.

Yet another embodiment of the invention relates to a method treat cancer that expresses Brachyury. In one aspect, the method comprises administering to a subject with a cancer that expresses Brachyury a yeast-Brachyury immunotherapeutic composition as described above or elsewhere herein.

Yet another embodiment of the invention relates to a method to reduce, arrest, reverse, delay or prevent the metastatic progression of cancer in an individual who has cancer, comprising administering to an individual who has a cancer that is undergoing metastatic progression, is at risk of undergoing metastatic progression, or is predicted to begin undergoing metastatic progression, the immunotherapeutic composition as described above or elsewhere herein.

Still another embodiment of the invention relates a method to prevent or delay the onset of a Brachyury-expressing cancer, comprising administering to an individual the immunotherapeutic composition as described above or elsewhere herein.

Another embodiment of the invention relates to method to treat chordoma, comprising administering to a subject who has chordoma the immunotherapeutic composition as described above or elsewhere herein.

In one aspect of any of the embodiments or aspects of the invention described above or elsewhere herein, the individual is being treated or has been treated with another therapy for cancer. In one aspect, the therapy is selected from radiation therapy, surgical resection of a tumor, chemotherapy, targeted cancer therapy, adoptive T cell transfer, or administration of one or more additional immunotherapeutic compositions.

Another embodiment of the invention relates to a method to reduce or prevent chemotherapy-resistance or radiation-resistance of tumor cells in a patient with cancer, comprising administering to an individual who has cancer and is receiving chemotherapy and/or radiation therapy an immunotherapeutic composition as described above or elsewhere herein.

In one aspect of any of the embodiments or aspects of the invention described above or elsewhere herein, the method reduces tumor burden in the individual, increases survival of the individual, and/or inhibits tumor growth in the individual. In one aspect, the cancer is breast cancer, bone cancer, chordoma, small intestine cancer, stomach cancer, pancreatic cancer, kidney cancer, bladder cancer, uterine cancer, ovarian cancer, testicular cancer, lung cancer, colon cancer, prostate cancer, chronic lymphocytic leukemia (CLL), Burkitt's lymphoma, Hodgkin's lymphoma, and metastatic cancers thereof.

Another embodiment of the invention relates to method to treat or prevent a disease or condition associated with Epstein Barr Virus (EBV) infection, comprising administering to an individual a yeast-Brachyury immunotherapeutic composition as described above or elsewhere herein.

Yet another embodiment of the invention relates to the use of any of the immunotherapeutic compositions described herein to treat a cancer that expresses Brachyury; to reduce, arrest, reverse or prevent the metastatic progression of cancer in an individual who has cancer; to prevent or delay the onset of a Brachyury-expressing cancer or to reduce or prevent chemotherapy-resistance or radiation-resistance of tumor cells in a patient with cancer.

Still another embodiment of the invention relates to the use of any of the immunotherapeutic compositions described herein in the preparation of a medicament for treating a cancer that expresses Brachyury.

DETAILED DESCRIPTION OF THE INVENTION

Figure 1:
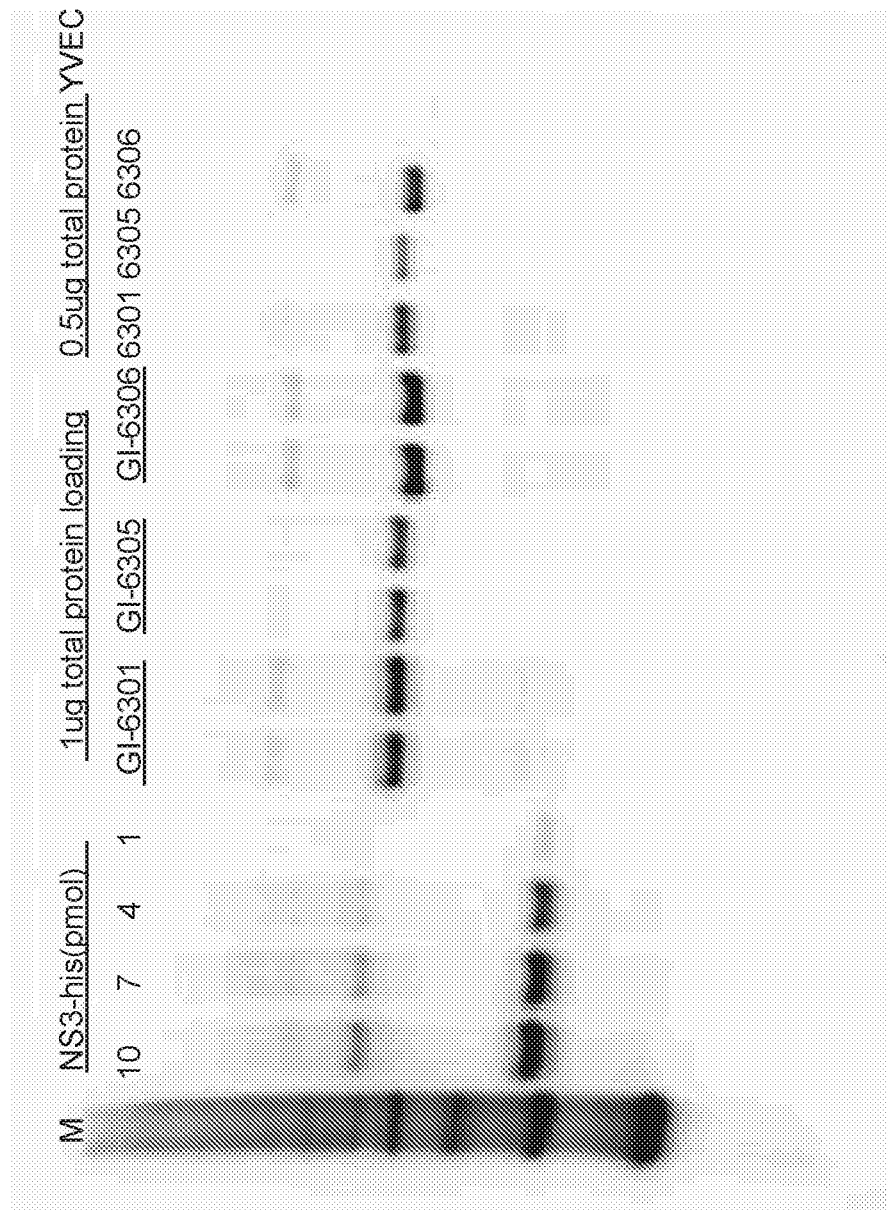
FIG. 1 is a digital image of a Western blot showing antigen expression of a yeast-Brachyury immunotherapeutic composition known as GI-6306 (or 6306) compared to antigen expression in the yeast-Brachyury immunotherapeutic compositions denoted GI-6301 (or 6301) and GI-6305 (or 6305). ("ug" is micrograms). "YVEC" is empty vector yeast.

This invention generally relates to improved yeast-Brachyury immunotherapeutic compositions, methods for producing such compositions, and methods for the prevention and/or treatment of cancers that express or overexpress Brachyury using such compositions. The invention includes specific modifications to the Brachyury antigen that create a novel Brachyury antigen with reduced or disrupted DNA binding activity for use in immunotherapy. The inventors have made the surprising and unexpected discovery that such modifications to the Brachyury antigen also improve both the manufacture and use of yeast-Brachyury immunotherapeutic compositions. Yeast-Brachyury immunotherapy compositions of the invention not only lack the ability to bind DNA and therefore act as a transcription factor as does native Brachyury, but they are surprisingly and unexpectedly also easier to manufacture, easier to administer, and express the Brachyury antigen at high levels, even when other modifications are introduced (e.g., agonist mutations).

More specifically, the invention includes improved yeast-based immunotherapeutic compositions (also referred to herein as "yeast-based immunotherapy", "yeast-Brachyury immunotherapy", "yeast-Brachyury immunotherapeutic compositions", "yeast-based immunotherapy product", "yeast-based vaccine", or derivatives of these phrases), wherein the composition comprises a yeast vehicle and at least one modified Brachyury antigen (including a Brachyury agonist antigen), wherein the DNA binding activity of the Brachyury antigen (e.g., as compared to a wild-type Brachyury protein) has been reduced or abolished by mutation (e.g., by deletion, substitution, insertion or other modification within the Brachyury DNA binding region sufficient to reduce or abolish the natural DNA binding activity of the Brachyury protein). The invention further includes uses of these improved yeast-Brachyury immunotherapeutic compositions to treat or prevent cancers, as well as methods of producing these improved yeast-Brachyury immunotherapeutic compositions. The inventors describe herein the construction and production of these novel yeast-Brachyury immunotherapy products, which are designed to expand Brachyury-specific T cells, including CD4$^+$ T cells and CD8$^+$ CTLs, from normal individuals and from cancer patients. Yeast-Brachyury immunotherapy using the novel compositions of the invention is useful for the elicitation of Brachyury-specific cellular immune responses (CD4$^+$ and CD8$^+$) and for administration to subjects with Brachyury-expressing tumors, offering novel therapy for the prevention and/or treatment of cancers expressing Brachyury, including, but not limited to chordomas, metastatic cancers and associated conditions.

Since Brachyury is not expressed by most normal (non-tumor) tissues, and is typically over-expressed in tumor cells, any "off target" effects related to normal tissues are not of concern and have not been observed as of the time of the invention, where Brachyury antigens that retain their DNA binding sequences have been used in vivo. However, the improved yeast-Brachyury immunotherapeutic compositions of the invention contain modifications that abrogate the DNA binding function of the native Brachyury, thereby eliminating the ability of Brachyury antigen to act as a transcription factor and therefore any downstream affects of such activity. In the present invention, Brachyury needs only to act as an immunogen, and so the inactivation of its natural role in mRNA transcription is not problematic.

The inventors have made the unexpected and unpredictable discovery that when the Brachyury with abrogated DNA binding activity was expressed in yeast, the yeast had different structural characteristics as compared to yeast expressing Brachyury without this modification. More particularly, yeast-Brachyury compositions without the modification described by the present invention display a robust "flocculation" phenotype during the manufacturing process, meaning that as the yeast cells grow and express the Brachyury antigen, the cells aggregate into large multicellular structures which are denser than non-aggregated cells in the growth medium or PBS (described more particularly below). In contrast, yeast expressing the modified Brachyury antigen of the present invention do not exhibit the flocculation phenotype, or exhibit a substantially reduced flocculation phenotype. Accordingly, not only does abrogating the DNA binding function of Brachyury provide a yeast-based immunotherapy product that lacks natural Brachyury biological activity while maintaining immunogenicity of the antigen, a surprising and unexpected property of the new antigen is the loss of the flocculation phenotype in yeast expressing the modified antigen. Loss of the flocculation phenotype allows for the ability to reduce the number of steps and/or modify steps in the manufacturing process that are utilized to accommodate this characteristic in yeast-Brachyury.

In addition, an exemplary Brachyury antigen containing the modification of the invention (see Examples) was expressed at substantially higher levels in yeast as compared to the expression level of a Brachyury antigen that was identical in sequence except for the novel modification. This result indicated that the modification of Brachyury antigens according to the invention can also enhance Brachyury antigen expression in yeast. Robust antigen expression is a highly positive characteristic of a yeast-Brachyury immunotherapy composition.

Yeast-Brachyury immunotherapeutic compositions useful in the present invention target tumor cells before or at the time during which they begin to acquire motility and invade other tissues, thereby preventing, inhibiting, arresting, reversing or delaying the onset of metastatic cancer and/or the progression of cancer, and especially metastatic cancer. In addition, yeast-Brachyury immunotherapy compositions of the invention can be used to prevent or delay metastatic cancer or progression of cancer in individuals who have early stage cancer, or who have a precancerous (pre-malignant) lesion or tumor, in individuals who are at a high risk for developing a cancer, particularly one that has a high rate of metastases, and even in normal individuals as a prophylactic agent for the prevention of cancer, which may be used in conjunction with other prophylactic immunotherapy for cancer, such as described herein.

Yeast-Brachyury immunotherapy compositions of the invention also provide a benefit to individuals who are undergoing other therapy for cancer, including chemotherapy and radiation therapy. Metastatic cancers are known in some cases to be more resistant to chemotherapy and/or radiation therapy than the primary cancers. Therefore, the yeast-Brachyury immunotherapy compositions of the invention can be used to inhibit or reduce or eliminate chemotherapy resistance or radiation resistance that may occur in metastatic cancer by inhibiting Brachyury expressing tumors in the cancer (and thereby inhibiting anti-proliferative influences), and compositions of the invention may enhance the performance of chemotherapy or radiation therapy in an individual.

In recent years, Brachyury has become a discriminating biomarker for a rare bone cancer known as chordoma. When combined with cytokeratin staining, sensitivity and specificity for detection of chordomas using Brachyury is 98% and 100% respectively (Oakley et al. (2008), *Mod Path* 21, 1461-1469). Accordingly, yeast-Brachyury immunotherapy compositions of the present invention are useful for the prevention and/or treatment of chordomas.

Yeast-Brachyury immunotherapy compositions of the invention can also be used to treat conditions or diseases associated with Brachyury expression that may be non-oncological in nature, or that may precede malignant transformation. For example, Brachyury may be upregulated in cells that are infected with an infectious agent, e.g., a virus such as Epstein Barr Virus (EBV). Accordingly, yeast-Brachyury immunotherapy of the invention can be used to treat or prevent any disease or condition associated with Brachyury expression, including, but not limited to, infectious diseases, such as viral infection, including, but not limited to, EBV-associated conditions (e.g., mononucleosis).

Yeast-Brachyury compositions described herein induce innate immune responses, as well as adaptive immune responses against the target antigen (Brachyury), including CD4-dependent TH17 and TH1 T cell responses and antigen-specific CD8$^+$ T cell responses, which include cytotoxic T lymphocyte (CTL) responses, all without the use of exogenous adjuvants, cytokines, or other immunostimulatory molecules, many of which have toxicity issues. In addition, yeast-Brachyury immunotherapeutic compositions inhibit regulatory T cell (Treg) numbers and/or functionality, thereby enhancing effector T cell responses that might normally be suppressed by the presence of the tumor, for example. Moreover, as compared to immunotherapeutic compositions that immunize by generating antibody responses, the antigen-specific, broad-based, and potent cellular immune responses elicited by yeast-Brachyury immunotherapy are believed to be particularly effective in targeting tumor cells. Indeed, numerous studies have shown that immunotherapeutic approaches are enhanced when tumor cells are targeted via CD8$^+$ CTLs which recognize tumor peptides in the context of MHC Class I molecules.

Yeast-Brachyury immunotherapy is highly adept at activating antigen presenting cells, and has a unique ability to cross-prime the immune response, generating CD8$^+$ CTL responses that are typically effective against tumors, even in the face of what may otherwise be a suppressive environment. Since this type of immunotherapy utilizes the natural ability of the antigen presenting cell to present relevant immunogens, it is not necessary to know the precise identity of CTL epitopes or MHC Class II epitopes of Brachyury to produce an effective immunotherapeutic according to the present invention. In fact, multiple CD4$^+$ and CD8$^+$ T cell epitopes can be targeted in a single yeast-Brachyury immunotherapeutic composition, and so the yeast-Brachyury immunotherapeutics of the invention are not limited to the use of short peptides and in fact, the use of longer polypeptides and fusion proteins in these compositions is efficacious. Accordingly, by using yeast-Brachyury immunotherapy, the use of algorithms and complex formulas to identify putative T cell epitopes is eliminated.

Yeast-Brachyury can be effectively utilized in an immunization protocol (prophylactic or therapeutic) without the use of exogenous adjuvants, immunostimulatory agents or molecules, costimulatory molecules, or cytokines, although such agents may be included, if desired. Moreover, yeast-Brachyury immunotherapy can be administered repeatedly without losing efficacy, as may be problematic with other types of immunotherapy.

Compositions of the Invention

One embodiment of the present invention relates to a yeast-based immunotherapy composition which can be used to prevent and/or treat cancers or other diseases characterized by Brachyury expression or overexpression (including cancers that may not contain cells expressing detectable Brachyury initially, but which may or will contain cells expressing Brachyury at later stages of the development of the cancer). The composition is a yeast-Brachyury immunotherapeutic composition comprising: (a) a yeast vehicle; and (b) a cancer antigen comprising one or more Brachyury antigen(s), wherein the Brachyury antigen is a modified Brachyury antigen (e.g., as compared to a wild-type Brachyury protein). Specifically, the modified Brachyury antigen minimally comprises a modification where the DNA binding activity of the Brachyury protein has been reduced or abolished by mutation (e.g., by deletion, substitution, insertion or other modification of the Brachyury DNA binding region sufficient to reduce or abolish the natural DNA binding activity of the Brachyury protein). In one aspect, the modified Brachyury antigen minimally comprises a modification that results in yeast expressing the modified Brachyury antigen having a reduced flocculation phenotype (the yeast exhibit reduced aggregation into large multi-cellular structures), as compared to yeast expressing a wild-type Brachyury protein. The modified Brachyury antigen may include additional modifications (i.e., differences from a wild-type Brachyury protein), such as a substitution of one or more amino acid residues in the protein to create one or more agonist epitopes in the Brachyury antigen (described in more detail below). Finally, the modified Brachyury antigen, even though modified, retains the ability to elicit an immune response, and preferably a cell-mediated immune response (a T cell response) against a native Brachyury protein, such as a Brachyury protein expressed by a tumor cell. The modified Brachyury antigen is most typically expressed as a recombinant protein by the yeast vehicle (e.g., by an intact (whole) yeast or yeast spheroplast, which can optionally be further processed to a yeast cytoplast, yeast ghost, or yeast membrane extract or fraction thereof), although it is an embodiment of the invention that one or more modified Brachyury antigens can be loaded into a yeast vehicle or otherwise complexed with, attached to, mixed with or administered with a yeast vehicle as described herein to form a composition of the present invention.

According to the present invention, a "yeast-Brachyury immunotherapeutic composition" is a specific type of "yeast-based immunotherapeutic composition" that contains a yeast vehicle and at least one Brachyury antigen or immunogenic domain thereof, and in the present invention, contains at least one modified Brachyury antigen as described above and elsewhere herein. An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and typically, an antigen component, and can elicit or induce an immune response, such as a cellular immune response, including without limitation a T cell-mediated cellular immune response. In one aspect, a yeast-based immunotherapeutic composition useful in the invention is capable of inducing a $CD8^+$ and/or a $CD4^+$ T cell-mediated immune response and in one aspect, a $CD8^+$ and a $CD4^+$ T cell-mediated immune response, particularly against a target antigen (e.g., a cancer antigen). A $CD4^+$ immune response can include TH1 immune responses, TH2 immune responses, TH17 immune responses, or any combination of the above. Yeast-based immunotherapeutics are particularly capable of generating TH1 and TH17 responses. A $CD8^+$ immune response can include a cytotoxic T lymphocyte (CTL) response, and yeast-based immunotherapeutics are capable of generating such responses. In one aspect, a yeast-based immunotherapeutic composition modulates the number and/or functionality of regulatory T cells (Tregs) in a subject. Yeast-based immunotherapy can also be modified to promote one type of response over another, e.g., by the addition of cytokines, antibodies, and/or modulating the manufacturing process for the yeast. Optionally, a yeast-based immunotherapeutic composition is capable of eliciting a humoral immune response.

Yeast-Brachyury immunotherapeutic compositions of the invention may be either "prophylactic" or "therapeutic". When provided prophylactically, the compositions of the present invention are provided in advance of the development of, or the detection of the development of, a cancer that expresses Brachyury, with the goal of preventing, inhibiting or delaying the development of Brachyury-expressing tumors; and/or preventing, inhibiting or delaying tumor migration and/or tumor invasion of other tissues (metastases) and/or generally preventing or inhibiting progression of cancer in an individual. As discussed herein, Brachyury is expressed in several cancers, including late-stage cancers, and has been shown to be involved in the EMT process, which is a process associated with invasiveness and migration of tumors, such as in metastatic cancer. Therefore, prophylactic compositions can be administered to individuals that appear to be cancer-free (healthy, or normal, individuals), to individuals with pre-cancerous (pre-malignant lesions), and also to individuals who have cancer, but in which Brachyury has not yet been detected (i.e. prior to the expression of Brachyury by tumor cells in the cancer). Individuals who are at high risk for developing a cancer, particularly a cancer with which Brachyury expression and/or metastases are typically associated, may be treated prophylactically with a composition of the invention. When provided therapeutically, the immunotherapy compositions are provided to an individual with a Brachyury-expressing cancer, with the goal of ameliorating the cancer, such as by reducing tumor burden in the individual; inhibiting tumor growth in the individual; increasing survival of the individual; preventing, inhibiting, reversing or delaying development of tumor migration and/or tumor invasion of other tissues (metastatic cancer) and/or preventing, inhibiting, reversing or delaying progression of the cancer in the individual. In one aspect, yeast-Brachyury immunotherapy is used therapeutically to inhibit, reduce or eliminate chemotherapy resistance or radiation resistance that may occur in metastatic cancer by inhibiting Brachyury expression in the cancer, and compositions of the invention may enhance the performance of chemotherapy or radiation therapy in an individual.

Typically, a yeast-Brachyury immunotherapy composition includes a yeast vehicle and at least one cancer antigen comprising a modified Brachyury antigen of the invention, where the cancer antigen is expressed by, attached to, loaded into, or mixed with the yeast vehicle. In some embodiments, the cancer antigen is provided as a fusion protein. Several modified Brachyury proteins and fusion proteins suitable for use in the compositions and methods of the invention are described below. In some embodiments, the cancer antigen and the modified Brachyury antigen are the same element. In some embodiments, the cancer antigen includes other antigens, including other cancer antigens, in addition to the modified Brachyury antigen. In one aspect of the invention, a fusion protein useful as a cancer antigen can include two or more antigens, e.g., a modified Brachyury antigen and another cancer antigen that is not a Brachyury antigen, or two different Brachyury antigens (e.g., two modified Brachyury antigens having different agonist epitopes). In one aspect, the fusion protein can include two or more immunogenic domains of one or more antigens, such as two or more immunogenic domains of a modified Brachyury antigen (where the immunogenic domain comprises the modification of the invention).

According to the present invention, the general use herein of the term "antigen" refers: to any portion of a protein (e.g., peptide, partial protein, full-length protein), wherein the protein is naturally occurring or synthetically derived or designed, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies). An antigen can be as small as a single epitope, a single immunogenic domain or larger, and can include multiple epitopes or immunogenic domains. As such, the size of an antigen can be as small as about 8-11 amino acids (i.e., a peptide) and as large as: a full length protein, a multimer, a fusion protein, a chimeric protein, a whole cell, a whole microorganism, or any portions thereof (e.g., protein fragments (polypeptides) lysates of whole cells or extracts of microorganisms). In addition, antigens can include carbohydrates, which can be loaded into a yeast vehicle or into a composition of the invention.

Antigens useful in the yeast-Brachyury immunotherapeutic of the present invention are polypeptides, full-length proteins, multimers, fusion proteins and chimeric proteins, wherein in any of these aspects, the antigen includes at least one modified Brachyury antigen as described herein. For expression in yeast, an antigen that is a protein, such as a modified Brachyury antigen, is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or at least or greater than 25-50 amino acids in length, or at least or greater than 30-50 amino acids in length, or at least or greater than 35-50 amino acids in length, or at least or greater than 40-50 amino acids in length, or at least or greater than 45-50 amino acids in length, although smaller proteins may be expressed, and considerably larger proteins (e.g., hundreds of amino acids in length or even a few thousand amino acids in length) may be expressed. In one aspect, a full-length protein or a protein that is lacking between 1 and 20 amino acids from the N- and/or the C-terminus may be expressed. Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired, e.g., Brachyury in the present invention). A "cancer antigen" is an antigen that comprises at least one antigen that is associated with a cancer such as an antigen expressed by a tumor cell, such that targeting the antigen also targets the cancer. A cancer antigen can include one or more antigens from one or more proteins, including one or more tumor-associated proteins. A "Brachyury antigen" is an antigen derived, designed, or produced from a Brachyury protein. A "modified Brachyury antigen" according to the present invention is a Brachyury antigen comprising an amino acid sequence that differs from the corresponding wild-type Brachyury amino acid sequence by least one modification (e.g., deletion, substitution, insertion or other modification) sufficient to reduce or abolish the natural DNA binding activity of the Brachyury protein, as compared to a wild-type Brachyury protein, and/or to reduce or eliminate the flocculation phenotype of yeast expressing the modified Brachyury antigen (e.g., yeast expressing the modified antigen have a reduced tendency to aggregate into large multi-cellular structures, as compared to yeast expressing a wild-type protein). A modified Brachyury antigen may comprise additional modifications, such as one or more amino acid substitutions that form an agonist epitope.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, the immunogen elicits a cell-mediated immune response, including a $CD4^+$ T cell response (e.g., TH1, TH2 and/or TH17) and/or a $CD8^+$ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that can act as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

Brachyury (which may also be referred to as "T") is a highly conserved protein among multiple different animal species and is a transcription factor that contains a "T-box" domain or "T-domain", a DNA-binding domain motif shared among several different proteins, collectively called the T-box family of proteins. Human Brachyury was first cloned in 1996 (Edwards et al., supra). One nucleotide sequence encoding an exemplary wild-type human Brachyury is represented herein by SEQ ID NO:1, which is an mRNA sequence that was obtained from GENBANK® Accession No. NM_003181 (GI:19743811). SEQ ID NO:1 encodes a 435 amino acid wild-type human Brachyury protein, the amino acid sequence of which is represented here as SEQ ID NO:2 (also found in GENBANK® Accession No. NP_003172; GI:4507339). Within SEQ ID NO:2, positions 42-223 are designated as the T-box region (T-box domain), and the positions specifically associated with DNA binding are designated as the following positions of SEQ ID NO:2: 63, 65, 66, 67, 68, 69, 70, 72, 101, 162, 196, 197, 198, 204, 208, 211, 212, 213, 214, 215, 216, 217, 218, and 219.

Another exemplary wild-type human Brachyury protein is a variant of the human Brachyury protein of SEQ ID NO:2, and has the amino acid sequence of SEQ ID NO:4. SEQ ID NO:4, also a 435 amino acid protein, is encoded by a nucleotide sequence represented herein by SEQ ID NO:3. SEQ ID NO:4 is approximately 99% identical to SEQ ID NO:2 over the full-length of the protein. SEQ ID NO:4 differs from SEQ ID NO:2 at position 177 (Asp vs. Gly, respectively), position 368 (Thr vs. Ser, respectively) and position 409 (Asn vs. Asp, respectively). The T-box region (T-box domain) is located at positions 42-223, and the positions specifically associated with DNA binding are designated as the following positions of SEQ ID NO:4: 63, 65, 66, 67, 68, 69, 70, 72, 101, 162, 196, 197, 198, 204, 208, 211, 212, 213, 214, 215, 216, 217, 218, and 219.

The T-box domain (or T-box region) is generally defined within all "T-box proteins" as the minimal region within the T-box protein that is both necessary and sufficient for sequence-specific DNA binding. Members of the T-box family (proteins having this domain) bind to the DNA consensus sequence TCACACCT (Wilson and Conlon, *Genome Biology* 2002, 3(6):reviews3008). In Brachyury, the seminal member of the T-box family, positions 1-229 of the murine protein (e.g., positions 1-229) were initially described as comprising the entire T-box DNA binding domain (Kispert et al., *The EMBO Journal* 1993, 12(8) 3211-3220; Kispert et al., *The EMBO Journal* 1996, 14(19): 4763-4772), and deletion of as little as the N-terminal 17 amino acids of the murine protein markedly attenuated the DNA binding ability of the protein (Kispert et al., 1993, supra). Based on the conservation of residues among different T-box proteins, subsequent publications and public databases have more particularly described the DNA binding domain as generally spanning from about position 41 or 42 through about position 223 (e.g., see GENBANK® Accession No. NP_003172), corresponding to an approximate 180 amino acid domain, although domains with additional or fewer amino acids within positions 1 through 229 can also be found in the scientific literature. Amino acid residues of Brachyury that have been identified through crystal structure as being directly involved in DNA binding include (positions given with respect to SEQ ID NO:2 or SEQ ID NO:4): Lys66, Arg69, Arg70, Arg101, Lys103, Lys147, Asn150, Lys151, Ser162, Thr196, Ala197, Tyr198, Ile208, Asn211, Pro212, Phe213, Ala214, Lys215, Ala216, and Phe217 (see, e.g., Müller and Herrmann, 1997, *Nature* 389:884-888, FIG. 1). Amino acid residues of Brachyury that have been identified through crystal structure as being directly involved in dimerization of the Brachyury protein (which is the form in which the protein binds to DNA, and as such, these residues may also impact DNA binding) include (positions given with respect to SEQ ID NO:2 or SEQ ID NO:4): Met87, Pro127, Asp128, Ser129, Pro130, Asn131, Phe132, and Val175 (see, e.g., Müller and Herrmann, 1997, *Nature* 389:884-888, FIG. 1).

The T-box domain and particular DNA binding residues, protein dimerization residues, or other residues important for activity from other Brachyury sequences, including Brachyury sequences from other species, can be readily identified by comparison to these sequences. As used herein, reference to a "T-box domain" or "DNA binding domain" of any Brachyury protein described herein or known in the art and utilized in the invention generally refers to at least positions 41 to 223 of a human Brachyury protein (exemplified by these positions in SEQ ID NO:2 or SEQ ID NO:4), and may include up to positions 1 through 229 of a human Brachyury protein, or an additional 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 consecutive amino acids of the Brachyury sequence on the N-terminal end of the domain, or an additional 1, 2, 3, 4, 5, or 6 consecutive amino acids of the Brachyury sequence on the C-terminal end of the defined T-box domain (e.g., on either side of positions 41-223 of SEQ ID NOs: 2 or 4). Residues particularly associated with DNA binding include, with reference to the human Brachyury sequence (exemplified by SEQ ID NO:2 or SEQ ID NO:4): positions 66, 69, 70, 101, 103, 147, 150, 151, 162, 196, 197, 198, 208, 211, 212, 213, 214, 215, 216 and 217. Residues particularly associated with dimerization of the protein and which can impact DNA binding activity of Brachyury include, with reference to the human Brachyury sequence (exemplified by SEQ ID NO:2 or SEQ ID NO:4): positions 87, 127, 128, 129, 130, 131, 132, and 175.

According to the present invention, a modified Brachyury antigen with "reduced or disrupted DNA binding activity" generally refers to a modified Brachyury protein that, as compared to a wild-type (naturally occurring, unmodified) Brachyury protein, the modified Brachyury protein has an observable or detectable (by any suitable detection means) and preferably, significant, and more preferably statistically significant, reduced ability to bind to DNA, or to the sequence to which Brachyury T-box region is known to bind, under standard laboratory or physiological conditions. In one aspect, the modified Brachyury antigen has no detectable ability to bind its natural DNA target. DNA binding activity can be detected by a variety of assays known in the art, including by contacting modified Brachyury proteins with DNA in vitro or ex vivo or by detecting transcription factor activity that would result from DNA binding. For example, the modified Brachyury can be incubated under suitable conditions with oligonucleotides to which native Brachyury binds, and bound complexes can be immunoprecipitated and evaluated. As another example, a cell can be co-transfected with a nucleotide construct encoding the modified Brachyury and with a reporter plasmid, and reporter activity (e.g., enzyme activity) can be measured as a readout of the ability of the Brachyury to bind to DNA or to act as a transcription factor, which requires the ability of the Brachyury to bind to DNA. See, e.g., Kispert et al., 1993, supra, or Kispert et al., 1996, supra for examples of these types of assays. Other assays that measure protein-DNA binding are known in the art.

According to the present invention, a modified Brachyury antigen that is associated with a "reduced yeast flocculation phenotype" refers to a Brachyury protein having modifications that result in yeast expressing the modified Brachyury antigen having a reduced flocculation phenotype, i.e., yeast expressing the antigen have a reduced tendency to aggregate into large multi-cellular structures or clump together. As discussed above, yeast expressing wild-type (unmodified) Brachyury antigens have a robust flocculation phenotype during culture. Yeast "flocculation" has been described in the art, and is generally defined as the non-sexual aggregation of yeast cells, which allows separation of the yeast cells from the medium in which the yeast were grown. Yeast having a flocculation phenotype are more dense than yeast without this phenotype in the growth medium or buffer in which they are contained and may not readily remain in suspension. There are several theories regarding the biological mechanisms responsible for flocculation, which are reviewed, for example, in Domingues et al., *Biotechnol. Bioprocess Eng.* 2000, 5: 288-305. Regardless of the mechanism by which yeast flocculation occurs, the present invention reduces the flocculation phenotype of yeast expressing Brachyury antigens by describing modifications that can be made to the antigen that result in this property in yeast. Flocculation phenotype in yeast can be measured using any suitable detection method including, but not limited to, bond strength measurement, floc size measurement, determination of yeast settling rate, sedimentation testing, atomic force microscopy (AFM), Helm's assay, and modified Helm's assays (see, e.g., van Hamersveld et al., *J Inst. Brew.* 1996, 102:333-342; Soares et al., *J Inst. Brew.*, 1997, 103:93-98; D'Hautcourt and Smart, *J Am Soc Brew Chem.*, 1999, 57:123-128; Vidgren and Londesborough, *J Inst Brew.* 2011, 117:475-487).

In one embodiment of the invention, a modified Brachyury antigen (i.e., a Brachyury antigen in which the DNA binding activity as compared to the wild-type protein has been reduced or disrupted and/or a Brachyury antigen wherein yeast expressing the antigen have a reduced flocculation phenotype) has an amino acid sequence that differs from the wild-type Brachyury amino acid sequence by at least 1, 2, 3, 4, 5, 6, 7, 8, 9, 10, 11, 12, 13, 14, 15, 16, 17, 18, 19, 20, 21, 22, 23, 24 or more amino acid modifications (i.e., deletions, substitutions, insertions or other modifications to an amino acid residue) sufficient to reduce or disrupt the DNA binding activity of Brachyury and/or reduce the flocculation phenotype of yeast that express the modified Brachyury protein. Preferably, the number of modifications to the Brachyury sequence is minimized to those necessary to achieve the goals of reduced or disrupted DNA binding and/or reduced flocculation phenotype of yeast, while maximizing the retention of T cell epitopes within the Brachyury antigen (i.e., maintenance of Brachyury amino acid sequences containing T cell epitopes is preferred). In one aspect of the invention, such modifications are made within positions 1-229 of Brachury (positions corresponding to the positions in SEQ ID NO:2 or SEQ ID NO:4). In one aspect of the invention, such modifications are made within positions 18-229 of Brachury (positions corresponding to the positions in SEQ ID NO:2 or SEQ ID NO:4). In one aspect of the invention, such modifications are made within positions 66 and 217 of Brachyury (positions corresponding to the positions in SEQ ID NO:2 or SEQ ID NO:4). In one aspect, such modifications are made within positions 198-222 of Brachyury (positions corresponding to the positions in SEQ ID NO:2 or SEQ ID NO:4). In one aspect, such modifications result in the deletion or substitution of at least 1, 2, 3, 4, 5, 6, 7, 8, 9, 10, 11, 12, 13, 14, 15, 16, 17, 18, 19 or 20 amino acid residues selected from: Lys66, Arg69, Arg70, Arg101, Lys103, Lys147, Asn150, Lys151, Ser162, Thr196, Ala197, Tyr198, Ile208, Asn211, Pro212, Phe213, Ala214, Lys215, Ala216, Phe217 (positions corresponding to the positions in SEQ ID NO:2 or SEQ ID NO:4). In one aspect, such modifications alternatively or additionally result in the deletion or substitution of at least 1, 2, 3, 4, 5, 6, 7, or 8 amino acid residues selected from: Met87, Pro127, Asp128, Ser129, Pro130, Asn131, Phe132, and/or Val175 (positions corresponding to the positions in SEQ ID NO:2 or SEQ ID NO:4). In one aspect, such modifications are a substitution or a deletion of at least 1, 2, 3, 4, 5, 6, 7, 8, 9, 10, 11, 12, 13, 14, 15, 16, 17, 18, 19, 20, 21, 22, 23, 24 or more contiguous amino acids between positions 66 and 217 of Brachyury or, in one aspect, between positions 198 and 222 of Brachyury (positions corresponding to the positions in SEQ ID NO:2 or SEQ ID NO:4). In all cases, the modifications achieve the goals of reduced or disrupted DNA binding and/or reduced flocculation phenotype of yeast expressing the antigen.

As discussed above, Brachyury antigens useful in the present invention can include, in addition to the modifications described above, one or more further modifications that result in the formation of an agonist epitope within the antigen. As generally used herein, an "agonist" is any compound or agent, including without limitation small molecules, proteins, peptides, antibodies, nucleic acid binding agents, etc., that binds to a receptor or ligand and produces or triggers a response, which may include agents that mimic or enhance the action of a naturally occurring substance that binds to the receptor or ligand. When used in the context of a Brachyury antigen of the invention, including a modified Brachyury antigen, an "agonist" antigen or protein refers to an antigen or protein that comprises at least one T cell agonist epitope, which may also be referred to as a "mimotope". A mimotope peptide is a peptide that mimics the structure of a wild-type epitope and as an agonist, the mimotope mimics or enhances the action (biological function) of the natural epitope.

For example, the amino acid sequence of SEQ ID NO:5 (WLLPGTSTL) is a T cell epitope of a wild-type Brachyury protein. SEQ ID NO:5 is located at positions 246-254 of SEQ ID NO:2 or SEQ ID NO:4. The amino acid sequence of SEQ ID NO:6 (WLLPGTSTV) is a mimotope or agonist of the T cell epitope of SEQ ID NO:5. Therefore, in one aspect of the invention, a modified Brachyury antigen comprises an amino acid sequence of WLLPGTSTV (SEQ ID NO:6). In one aspect, the amino acid at position 4 of SEQ ID NO:6 (a proline or P) is substituted with a serine (S), a threonine (T), an isoleucine (I), or a valine (V).

In one aspect, the modified Brachyury antigen comprises an amino acid sequence of SQYPSLWSV (SEQ ID NO:7). In one aspect, the amino acid at position 2 of SEQ ID NO:7 (a glutamine or Q in this sequence) is substituted with a leucine (L). In one aspect, the amino acid at position 4 of SEQ ID NO:7 (a proline or P in this sequence) is substituted with a serine (S), threonine (T), leucine (L), or valine (V). In one aspect, the amino acid at position 7 of SEQ ID NO:7 (a tryptophan or W in this sequence) is substituted with a valine (V), leucine (L), isoleucine (I), serine (S), or threonine (T). In one aspect, the amino acid at position 9 of SEQ ID NO:7 (a valine or V in this sequence) is substituted with a leucine (L). An antigen comprising a sequence having any combination of one or more of these substitutions in SEQ ID NO:7 is contemplated by the invention.

In one aspect, the modified Brachyury antigen comprises an amino acid sequence of RLIASWTPV (SEQ ID NO:8). In one aspect, the amino acid at position 1 of SEQ ID NO:8 (an arginine or R in this sequence) is substituted with a tyrosine (Y) or a tryptophan (W). In one aspect, the amino acid at position 6 of SEQ ID NO:8 (a tryptophan or W in this sequence) is substituted with a valine (V), a lysine (L), an isoleucine (I), a serine (S), or a threonine (T). An antigen comprising a sequence having any combination of one or both of these substitutions in SEQ ID NO:8 is contemplated by the invention.

In one aspect, the modified Brachyury antigen comprises an amino acid sequence of AMYSFLLDFV (SEQ ID NO:9). In one aspect, the amino acid at position 2 of SEQ ID NO:9 (a methionine or M in this sequence) is substituted with a leucine (L).

In one embodiment of the invention, a modified Brachyury antigen is a protein comprising, consisting essentially of, or consisting of the amino acid sequence of SEQ ID NO:10. The protein of SEQ ID NO:10 is one example of a modified Brachyury antigen according to the invention, where the amino acid sequence differs from the amino acid sequence of the human Brachyury protein represented by SEQ ID NO:4 by a deletion of positions 198-222 (i.e., positions 198-222 of SEQ ID NO:4 are not present in SEQ ID NO:10). In other words, SEQ ID NO:10 is a single polypeptide consisting of positions 1-197 fused directly to positions 223-435 of SEQ ID NO:4. This modified Brachyury antigen has disrupted DNA binding ability and yeast expressing the antigen have a reduced flocculation phenotype, as compared to the Brachyury protein of SEQ ID NO:4. SEQ ID NO:12 is a fusion protein comprising the modified Brachyury protein of SEQ ID NO:10 (actually positions 2-410 of SEQ ID NO:10, since the N-terminal methionine of SEQ ID NO:10 is removed to accommodate the addition of an N-terminal peptide described below). SEQ ID NO:12 is a single polypeptide with the following sequence elements fused in frame from N- to C-terminus: (1) an N-terminal peptide to impart resistance to proteasomal degradation and stabilize expression in yeast (positions 1-6 of SEQ ID NO:12, having the amino acid sequence of Met-Ala-Asp-Glu-Ala-Pro which is also represented herein by SEQ ID NO:16); (2) a human Brachyury antigen consisting of positions 2-197 and 223-435 of SEQ ID NO:4, which can also be described as positions 2-410 of SEQ ID NO:10 (positions 7-415 of SEQ ID NO:12); and (3) a hexahistidine tag (positions 416-421 of SEQ ID NO:12). The amino acid sequence of SEQ ID NO:12 and the amino acid sequence of positions 2-410 of SEQ ID NO:10 are encoded by the polynucleotide sequence of SEQ ID NO:11.

In another embodiment of the invention, a modified Brachyury antigen is a protein comprising, consisting essentially of, or consisting of the amino acid sequence of SEQ ID NO:13. The protein of SEQ ID NO:13 is another example of a modified Brachyury antigen according to the invention, where the amino acid sequence differs from the amino acid sequence of the human Brachyury protein represented by SEQ ID NO:4 by: (1) a deletion of positions 198-222 (i.e., positions 198-222 of SEQ ID NO:4 are not present in SEQ ID NO:13); and (2) a substitution of the amino acid (leucine) located at position 254 in SEQ ID NO:4 (and located at position 229 of SEQ ID NO:13) with a valine. In other words, SEQ ID NO:13 is a single polypeptide consisting of positions 1-197 fused directly to positions 223-435 of SEQ ID NO:4, and including an amino acid modification that results in the introduction of an agonist epitope into SEQ ID NO:13. The leucine to valine substitution at position 254 (with respect to SEQ ID NO:4) creates a T cell agonist epitope in SEQ ID NO:13 at positions 221-229 of SEQ ID NO:13, that, without being bound by theory, is believed to induce enhanced T cell responses against Brachyury as compared to the wild-type epitope (positions 246 to 254 of SEQ ID NO:4). This agonist epitope is also represented herein by SEQ ID NO:6. This modified Brachyury antigen represented by SEQ ID NO:13 has disrupted DNA binding ability and yeast expressing the antigen have a reduced flocculation phenotype, as compared to the Brachyury protein of SEQ ID NO:4, and additional contains the agonist epitope to enhance T cell responses against the native Brachyury when this construct is administered to a subject in a yeast-Brachyury immunotherapeutic. SEQ ID NO:15 is a fusion protein comprising the modified Brachyury protein of SEQ ID NO:13 (actually positions 2-410 of SEQ ID NO:13, since the N-terminal methionine of SEQ ID NO:13 is removed to accommodate the addition of an N-terminal peptide described below). SEQ ID NO:15 is a single polypeptide with the following sequence elements fused in frame from N- to C-terminus: (1) an N-terminal peptide to impart resistance to proteasomal degradation and stabilize expression in yeast (positions 1-6 of SEQ ID NO:15, the amino acid sequence of which is also represented herein by SEQ ID NO:16); (2) a human Brachyury antigen consisting of positions 2-197 and 223-435 of SEQ ID NO:4 and further containing a substitution of a valine for the leucine at position 254 of SEQ ID NO:4, which can also be described as positions 2-410 of SEQ ID NO:13 (positions 7-415 of SEQ ID NO:15); and (3) a hexahistidine tag (positions 416-421 of SEQ ID NO:15). The amino acid sequence of SEQ ID NO:15 and the amino acid sequence of positions 2-410 of SEQ ID NO:13 is encoded by the polynucleotide sequence of SEQ ID NO:14. A yeast-based immunotherapy composition expressing this fusion protein is also referred to herein as GI-6306.

In another embodiment of the invention, a modified Brachyury antigen is a protein comprising, consisting essentially of, or consisting of an amino acid sequence that differs from the amino acid sequence of a wild-type Brachyury protein (e.g. SEQ ID NO:2, SEQ ID NO:4, or a corresponding sequence of a different human Brachyury protein) by a deletion of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three or at least twenty-four amino acids, wherein the amino acid residues that may be deleted are selected from: (1) one or more amino acids selected from (positions given with respect to SEQ ID NO:2 or SEQ ID NO:4): Lys66, Arg69, Arg70, Arg101, Lys103, Lys147, Asn150, Lys151, Ser162, Thr196, Ala197, Tyr198, Ile208, Asn211, Pro212, Phe213, Ala214, Lys215, Ala216, Phe217, Met87, Pro127, Asp128, Ser129, Pro130, Asn131, Phe132, and/or Val175, with deletions at one or more of positions Lys66, Arg69, Arg70, Arg101, Lys103, Lys147, Asn150, Lys151, Ser162, Thr196, Ala197, Tyr198, Ile208, Asn211, Pro212, Phe213, Ala214, Lys215, Ala216, Phe217, being more preferred (positions corresponding to the positions in SEQ ID NO:2 or SEQ ID NO:4); (2) one or more amino acids located within positions 1-229 of the wild-type Brachyury protein (positions corresponding to the positions in SEQ ID NO:2 or SEQ ID NO:4); (3) one or more amino acids located within positions 66-217 of the wild-type Brachyury protein (positions corresponding to the positions in SEQ ID NO:2 or SEQ ID NO:4); or (4) one or more amino acids located within positions 198-222 of the wild-type Brachyury protein (positions corresponding to the positions in SEQ ID NO:2 or SEQ ID NO:4). In all cases, the modified Brachyury antigen has a reduced or disrupted DNA binding activity and/or yeast expressing the antigen have a reduced flocculation phenotype. In one aspect, the modified Brachyury antigen may be a "near-full length" Brachyury protein as defined below, meaning that the protein may be lacking between 1 and 10 amino acids from the N- and/or C-terminus as compared to the wild-type sequence.

In one aspect, the modified Brachyury antigen further comprises at least one agonist epitope (e.g., SEQ ID NO:6, or any other agonist epitope, such as the agonists of sequences of SEQ ID NOs:5, 7, 8, or 9 as described above).

In one aspect, the modified Brachyury antigen is part of a fusion protein, which in addition to the modified Brachyury antigen described above, may optionally also include: (1) an N-terminal peptide that is a synthetic N-terminal peptide designed to impart resistance to proteasomal degradation and stabilize expression represented by SEQ ID NO:16, which may be substituted by an N-terminal peptide such as a yeast alpha factor sequence, or another N-terminal peptide suitable for use with a yeast-based immunotherapeutic as described herein; (2) a C-terminal peptide useful for isolation or identification of the fusion protein, such as a hexahistidine tag; (3) a linker peptide of one, two, three or more amino acids used to join segments within the fusion protein; and/or (4) another antigen, which may be another Brachyury antigen or a different (non-Brachyury) antigen, and is preferably a cancer antigen.

In another embodiment of the invention, a modified Brachyury antigen is a protein comprising, consisting essentially of, or consisting of an amino acid sequence that differs from the amino acid sequence of a wild-type Brachyury protein (e.g. SEQ ID NO:2, SEQ ID NO:4, or a corresponding sequence of a different human Brachyury protein) by a substitution of at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three or at least twenty-four amino acids, with a different amino acid residue than the one that naturally occurs at that position. The amino acid residues that may be substituted are selected from: (1) one or more amino acids selected from (positions given with respect to SEQ ID NO:2 or SEQ ID NO:4): Lys66, Arg69, Arg70, Arg101, Lys103, Lys147, Asn150, Lys151, Ser162, Thr196, Ala197, Tyr198, Ile208, Asn211, Pro212, Phe213, Ala214, Lys215, Ala216, Phe217, Met87, Pro127, Asp128, Ser129, Pro130, Asn131, Phe132, and/or Val175, with substitutions at one or more of positions Lys66, Arg69, Arg70, Arg101, Lys103, Lys147, Asn150, Lys151, Ser162, Thr196, Ala197, Tyr198, Ile208, Asn211, Pro212, Phe213, Ala214, Lys215, Ala216, Phe217, being more preferred (positions corresponding to the positions in SEQ ID NO:2 or SEQ ID NO:4); (2) one or more amino acids located within positions 1-229 of the wild-type Brachyury protein (positions corresponding to the positions in SEQ ID NO:2 or SEQ ID NO:4); (3) one or more amino acids located within positions 66-217 of the wild-type Brachyury protein (positions corresponding to the positions in SEQ ID NO:2 or SEQ ID NO:4); or (4) one or more amino acids located within positions 198-222 of the wild-type Brachyury protein (positions corresponding to the positions in SEQ ID NO:2 or SEQ ID NO:4). In all cases, the substitutions result in a modified Brachyury antigen has a reduced or disrupted DNA binding activity and/or a yeast expressing the antigen have a reduced flocculation phenotype. In one aspect, the modified Brachyury antigen may be a "near-full length" Brachyury protein as defined below, meaning that the protein may be lacking between 1 and 10 amino acids from the N- and/or C-terminus as compared to the wild-type sequence. In one aspect, the modified Brachyury antigen further comprises at least one agonist epitope (e.g., SEQ ID NO:6, or any other agonist epitope, such as the agonists of sequences of SEQ ID NOs:5, 7, 8, or 9 as described above). In one aspect, the modified Brachyury antigen is part of a fusion protein, which in addition to the modified Brachyury antigen described above, may optionally also include: (1) an N-terminal peptide that is a synthetic N-terminal peptide designed to impart resistance to proteasomal degradation and stabilize expression represented by SEQ ID NO:16, which may be substituted by an N-terminal peptide such as a yeast alpha factor sequence, or another N-terminal peptide suitable for use with a yeast-based immunotherapeutic as described herein; (2) a C-terminal peptide useful for isolation or identification of the fusion protein, such as a hexahistidine tag; (3) a linker peptide of one, two, three or more amino acids used to join segments within the fusion protein; and/or (4) another antigen, which may be another Brachyury antigen or a different (non-Brachyury) antigen, and is preferably a cancer antigen.

Human Brachyury has very high homology with Brachyury from other animal species and therefore, one is able to utilize the sequences of Brachyury from other organisms, or human Brachyury sequences that differ from the exemplary human sequences described herein, in the preparation of a yeast-Brachyury immunotherapeutic composition of the invention, particularly where these sequences are identical, substantially homologous, and elicit an effective immune response against the target antigen (e.g., native Brachyury expressed by a tumor cell). For example, murine Brachyury, which was first cloned by Hermann and colleagues in 1990 (Hermann et al., supra) is approximately 85% identical to human Brachyury at the nucleotide level, and approximately 91% identical at the amino acid level. With respect to Brachyury from other animals, at the amino acid level, human Brachyury is 99.5% identical to Brachyury from *Pan troglodytes*, 90.1% identical to Brachyury from *Canis lupus familiaris*, 88.5% identical to Brachyury from *Bos Taurus*, 92.2% identical to Brachyury from *Rattus norvegicus*, and 80.9% identical to Brachyury from *Gallus*. Within amino acids 1-223 of Brachyury, which contains the T-box domain, mouse and human Brachyury differ by only two amino acids (at positions 26 and 96).

According to any embodiment of the present invention, reference to a "full-length" protein (or a full-length functional domain or full-length immunological domain) includes the full-length amino acid sequence of the protein or functional domain or immunological domain, as described herein or as otherwise known or described in a publicly available sequence. A protein or domain that is "near full-length", which is also a type of homologue of a protein, differs from a full-length protein or domain, by the deletion or omission of 1, 2, 3, 4, 5, 6, 7, 8, 9, or 10 amino acids from the N- and/or C-terminus of such a full-length protein or full-length domain. By way of example, several of the fusion proteins described herein comprise a "near full-length" Brachyury antigen since the antigen omits the methionine at position 1 and substitutes an N-terminal peptide. General reference to a protein or domain or antigen can include both full-length and near full-length proteins, as well as other homologues thereof.

In one aspect of any embodiments related to a Brachyury antigen or a cancer antigen, the antigen is of a minimum size sufficient to allow the antigen to be expressed by yeast. For expression in yeast, a protein is typically at least about 25 amino acids in length, although smaller proteins may be expressed, and considerably larger proteins may be expressed by yeast. For example, a cancer antigen useful in the invention is a fragment of a cancer protein that can be expressed recombinantly by yeast and that contains at least one immunogenic domain. In one embodiment, a cancer antigen useful in the present invention is at least 25 amino acids in length, or at least: 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, or 410, 415, 420, 425, or 430 amino acids in length.

A Brachyury antigen (including a modified Brachyury antigen) useful in the present invention also includes proteins having an amino acid sequence that is at least 85%, 86%, 87%, 88%, 89%, 90%, 91%, 92%, 93%, 94%, 95%, 96%, 97%, 98%, or 99% identical to the amino acid sequence of any of the modified Brachyury antigens described herein (e.g., SEQ ID NO:10, SEQ ID NO:12, SEQ ID NO:13 or SEQ ID NO:15) over the full length of the protein, wherein the Brachyury antigen retains the characteristics of a modified Brachyury antigen of the invention (i.e., reduced or disrupted DNA binding activity and/or yeast expressing the antigen have a reduced flocculation phenotype).

As discussed briefly above, N-terminal expression sequences and the C-terminal tags, such as those described above with respect to the fusion proteins described herein are optional, but may be selected from several different sequences described elsewhere herein to improve or assist with expression, stability, and/or allow for identification and/or purification of the protein. Also, many different promoters suitable for use in yeast are known in the art. Furthermore, short intervening linker sequences (e.g., 1, 2, 3, 4, or 5 amino acid peptides) may be introduced between portions of a fusion protein comprising a Brachyury antigen for a variety of reasons, including the introduction of restriction enzyme sites to facilitate cloning, as cleavage sites for host phagosomal proteases, to accelerate protein or antigen processing, and for future manipulation of the constructs.

Optionally, proteins, including fusion proteins, which are used as a component of the yeast-Brachyury immunotherapeutic composition of the invention are produced using antigen constructs that are particularly useful for improving or stabilizing the expression of heterologous antigens in yeast. In one embodiment, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to yeast alpha factor leader sequence, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). An exemplary synthetic sequence that enhances the stability of expression of an antigen in a yeast cell and/or prevents post-translational modification of the protein in the yeast includes the sequence M-A-D-E-A-P (represented herein by SEQ ID NO:16). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His or hexapeptide) or any other short epitope tag. Peptides attached to the C-terminus of an antigen according to the invention can be used with or without the addition of the N-terminal peptides discussed above, and vice versa.

According to the present invention, a yeast vehicle used in a yeast-Brachyury immunotherapy composition is any yeast cell (e.g., a whole or intact cell) or a derivative thereof (see below) that can be used in conjunction with one or more antigens, immunogenic domains thereof or epitopes thereof in a composition of the invention (e.g., a therapeutic or prophylactic composition). The yeast vehicle can therefore include, but is not limited to, a live intact (whole) yeast microorganism (i.e., a yeast cell having all its components including a cell wall), a killed (dead) or inactivated intact yeast microorganism, or derivatives of intact yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674, incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, non-pathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe*. *S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. Another yeast strain is useful in the invention is *Saccharomyces cerevisiae* W303α. In addition, any mutant yeast strains can be used in the present invention, including those that exhibit reduced post-translational modifications of expressed target antigens or other proteins, such as mutations in the enzymes that extend N-linked glycosylation.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In general, the yeast vehicle and antigen(s) (and/or other agents) can be associated with each other by any technique described herein. In one aspect, the yeast vehicle was loaded intracellularly with the antigen(s). In another aspect, the antigen(s) was covalently or non-covalently attached to the yeast vehicle. In yet another aspect, the yeast vehicle and the antigen(s) were associated by mixing. In another aspect, which is a preferred embodiment, the antigen(s) are expressed recombinantly by the yeast vehicle or by the yeast cell or yeast spheroplast from which the yeast vehicle was derived.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein (s) are being used, one of skill in the art will select a spacer arm that effectuates appropriate spacing for the antigen or other protein on the yeast surface. In one embodiment, the spacer arm is a yeast protein of at least 450 amino acids.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast. The yeast cell can then be formulated with a pharmaceutically acceptable excipient and administered directly to a patient, stored for later administration, or loaded into a dendritic cell as an intact cell. The yeast cell can also be killed, or it can be derivatized such as by formation of yeast spheroplasts, cytoplasts, ghosts, or subcellular particles, any of which may be followed by storing, administering, or loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses the antigen. Yeast cells or yeast spheroplasts that recombinantly express the antigen(s) may be used to produce a yeast vehicle comprising a yeast cytoplast, a yeast ghost, or a yeast membrane particle or yeast cell wall particle, or fraction thereof.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PHO5), including hybrid promoters such as ADH2/ GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego). For example, under one protocol, liquid cultures containing a suitable medium can be inoculated using cultures obtained from starter plates and/or starter cultures of yeast-Brachyury immunotherapy compositions, and are grown for approximately 20 h at 30° C., with agitation at 250 rpm. Primary cultures can then be expanded into larger cultures as desired. Protein expression from vectors with which the yeast were transformed (e.g., Brachyury expression) may be constitutive if the promoter utilized is a constitutive promoter, or may be induced by addition of the appropriate induction conditions for the promoter if the promoter utilized is an inducible promoter (e.g., copper sulfate in the case of the CUP1 promoter). In the case of an inducible promoter, induction of protein expression may be initiated after the culture has grown to a suitable cell density, which may be at about 0.2 Y.U./ml or higher densities.

One non-limiting example of a medium suitable for the culture of a yeast-Brachyury immunotherapy composition of the invention is U2 medium. U2 medium comprises the following components: 20 g/L of glucose, 6.7 g/L of Yeast nitrogen base containing ammonium sulfate, and 0.04 mg/mL each of histidine, leucine, tryptophan, and adenine. Another non-limiting example of a medium suitable for the culture of yeast-Brachyury immunotherapy composition of the invention is UL2 medium. UL2 medium comprises the following components: 20 g/L of glucose, 6.7 g/L of Yeast nitrogen base containing ammonium sulfate, and 0.04 mg/mL each of histidine, tryptophan, and adenine.

When an inducible promoter is used (e.g. the CUP1 promoter) to express a modified Brachyury antigen in a yeast vehicle according to the invention, induction of protein expression is initiated at a higher cell density as compared to the cell density that would be suitable for most proteins expressed by yeast using such a promoter. Optimal Brachyury antigen expression driven by the CUP1 promoter occurs when the yeast expressing the Brachyury antigen are allowed to grow to a cell density of between at least 0.5 Y.U/ml and approximately 2.0 Y.U./ml, and in one aspect, to between 0.5 Y.U./ml and approximately 1.5 Y.U./ml, and in one aspect, to between at least 1.0 Y.U./ml and about 2.0 Y.U./ml, and in another aspect, to at least about 1.0 Y.U./ml, prior to inducing expression of the Brachyury antigen in the yeast. In one embodiment of the invention, a yeast-Brachyury immunotherapy composition having antigen expression under the control of an inducible promoter, such as the CUP1 promoter, is grown to mid-log phase prior to inducing antigen expression. In one aspect, the cells are grown to between about 1 and 2 Y.U./ml prior to induction of antigen expression. In one aspect, antigen expression is induced (e.g., by the addition of copper sulfate) and continues for up to 6, 6.5, 7, 7.5, or 8 hours. In one aspect, the induction occurs at a temperature of about 30° C. and agitation rate of 250 rpm.

In some embodiments of the invention, the yeast are grown under neutral pH conditions. As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5 or 8. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The yeast can continue to grow to high densities without losing their cell wall pliability. The use of a neutral pH allows for the production of yeast with pliable cell walls and/or yeast that are more sensitive to cell wall digesting enzymes (e.g., glucanase) at all harvest densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., TH1-type cytokines including, but not limited to, IFN-γ, interleukin-12 (IL-12), and IL-2, as well as proinflammatory cytokines such as IL-6). In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5).

In one embodiment of the invention, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include modified Brachyury antigens of the invention (e.g., as a protein subunit or contained within a different vehicle) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-α) or agonists or antagonists of type I interferon or a receptor thereof; type II interferon (including IFN-γ) or agonists or antagonists of type II interferon or a receptor thereof; anti-CD40, CD40L, lymphocyte-activation gene 3 (LAG3) protein and/or IMP321 (T-cell immunostimulatory factor derived from the soluble form of LAG3), anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; immune checkpoint inhibitors (e.g., inhibitors of "immune checkpoints" which are inhibitory pathways of the immune system that maintain self-tolerance and modulate the duration and amplitude of physiological immune responses, such immune checkpoint inhibitors including but not limited to: anti-CTLA-4 antibody, such as ipilimumab (Bristol-Myers Squibb, Princeton, N.J.) or tremelimumab (MedImmune/AstraZeneca, Wilmington, Del.), programmed cell death protein 1 (PD-1), programmed cell death protein 1 ligand (PD-L1), programmed cell death protein 2 ligand (PD-L2, such as the PD-L2 fusion protein known as AMP-224 (Amplimmune, Gaithersburg, Md./GlaxoSmithKline, Philadelphia, Pa.)), anti-PD-1 antibody (such as nivolumab (Bristol-Myers Squibb), pembrolizumanb (Merck, Whitehouse Station, N.J.), or pidilizumab (CureTech, Yavne, Israel)), anti-PD-L1 antibody (such as MPDL3280A (Genentech, South San Francisco, Calif.), MEDI4736 (MedImmune/AstraZeneca), BMS-936559 (Bristol-Myers Squibb), MSB0010718C (EMD Serono, Rockland, Md.)), or anti-PD-L2 antibody); indoleamine 2,3-dioxygenase (IDO) inhibitors (such as INCB24360); agents that block FOXP3 (e.g., to abrogate the activity/kill CD4+/CD25+ T regulatory cells); Flt3 ligand, imiquimod (Aldara™), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, proinflammatory agents, and any agents that modulate the number of, modulate the activation state of, and/or modulate the survival of antigen-presenting cells or of TH17, TH1, and/or Treg cells. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Compositions of the invention can further include or can be administered with (concurrently, sequentially, or intermittently with) any other agents or compositions or protocols that are useful for preventing or treating cancer or any compounds that treat or ameliorate any symptom of cancer, and particularly cancers associated with Brachyury expression or overexpression. In addition, compositions of the invention can be used together with other immunotherapeutic compositions, including prophylactic and/or therapeutic immunotherapy. Indeed, the compositions of the invention can be used to inhibit or reduce chemotherapy resistance or radiation resistance that may occur in metastatic cancer by inhibiting Brachyury expression in the cancer (and thereby inhibiting anti-proliferative influences) or compositions of the invention may enhance the performance of chemotherapy or radiation therapy in an individual. Additional agents, compositions or protocols (e.g., therapeutic protocols) that are useful for the treatment of cancer include, but are not limited to, chemotherapy, surgical resection of a tumor, radiation therapy, allogeneic or autologous stem cell transplantation, and/or targeted cancer therapies (e.g., small molecule drugs, biologics, or monoclonal antibody therapies that specifically target molecules involved in tumor growth and progression, including, but not limited to, selective estrogen receptor modulators (SERMs), aromatase inhibitors, tyrosine kinase inhibitors, serine/threonine kinase inhibitors, histone deacetylase (HDAC) inhibitors, retinoid receptor activators, apoptosis stimulators, angiogenesis inhibitors, poly (ADP-ribose_) polymerase (PARP) inhibitors, or immunostimulators). Any of these additional therapeutic agents and/or therapeutic protocols may be administered before, concurrently with, alternating with, or after the immunotherapy compositions of the invention, or at different time points. For example, when given to an individual in conjunction with chemotherapy or a targeted cancer therapy, it may be desirable to administer the yeast-Brachyury immunotherapy compositions during the "holiday" between doses of chemotherapy or targeted cancer therapy, in order to maximize the efficacy of the immunotherapy compositions. Surgical resection of a tumor may frequently precede administration of a yeast-Brachyury immunotherapy composition, but additional or primary surgery may occur during or after administration of a yeast-Brachyury immunotherapy composition.

The invention also includes a kit comprising any of the compositions described herein, or any of the individual components of the compositions described herein. Kits may include additional reagents and written instructions or directions for using any of the compositions of the invention to prevent or treat cancer associated with Brachyury expression or overexpression.

Methods for Administration or Use of Compositions of the Invention

Yeast-Brachyury immunotherapeutic compositions of the invention are designed for use to prevent or treat cancers that are associated with or characterized by Brachyury expression or overexpression, including by preventing emergence of such cancers, arresting progression of such cancers or ameliorating or eliminating such cancers. More particularly, yeast-Brachyury immunotherapeutic compositions can be used to prevent, inhibit or delay the development of Brachyury-expressing tumors, and/or to prevent, inhibit or delay tumor migration and/or tumor invasion of other tissues (metastases) and/or to generally prevent or inhibit progression of cancer in an individual. Yeast-Brachyury immunotherapeutic compositions can also be used to ameliorate at least one symptom of a cancer, such as by reducing tumor burden in the individual; inhibiting tumor growth in the individual; increasing survival of the individual; preventing, inhibiting, reversing or delaying development of tumor migration and/or tumor invasion of other tissues (metastatic cancer) and/or preventing, inhibiting, reversing or delaying progression of the cancer in the individual. Yeast-Brachyury immunotherapy can also be used therapeutically to inhibit, reduce or eliminate chemotherapy resistance or radiation resistance that may occur in metastatic cancer by inhibiting Brachyury expression in the cancer, and compositions of the invention may enhance the performance of chemotherapy or radiation therapy in an individual.

Cancers that are relevant to the compositions and methods of the invention are any cancer that expresses, or may express, Brachyury, or cancers in proximity to cancers that express or may express Brachyury, and include, but are not limited to, cancer of the breast, bone (including but not limited to chordomas), small intestine, stomach, kidney, bladder, uterus, ovary, testes, lung, colon, pancreas, or prostate, and include metastatic and late-stage cancers. In addition, Brachyury is expressed in tumors of B cell origin, such as chronic lymphocytic leukemia (CLL), Epstein-Barr virus transformed B cells, Burkitt's and Hodgkin's lymphomas, as well as metastatic cancers thereof.

Accordingly, one embodiment of the invention relates to a method to treat cancer, and particularly, a Brachyury-expressing cancer. The method includes administering to an individual who has a Brachyury-expressing cancer a yeast-Brachyury immunotherapeutic composition described herein, which includes a composition comprising: (a) a yeast vehicle; and (b) a cancer antigen comprising at least one modified Brachyury antigen of the invention. In one aspect, the method reduces tumor burden in the patient. In one aspect, the method increases survival of the patient. In one aspect, the method inhibits tumor growth in the individual. In one aspect, the method prevents, arrests or reverses metastatic progression of the tumor.

Since Brachyury expression is believed to be more prevalent as a cancer advances or progresses into higher stages (e.g., from stage I to stage II to stage III to stage IV, depending on the particular cancer) and is associated with metastatic processes, it is an embodiment of the invention to provide a method to prevent or delay the onset of a Brachyury-expressing cancer, or to arrest the cancer at a pre-metastatic or pre-malignant stage, or to prevent or delay the progression of such a cancer (e.g., to stabilize the cancer). Such a method includes administering to an individual in whom Brachyury-expressing cancer cells are not detected a yeast-Brachyury immunotherapeutic composition described herein, which can include a composition comprising: (a) a yeast vehicle; and (b) a cancer antigen comprising at least one modified Brachyury antigen of the invention. In one aspect of this embodiment, the cancer is known to express or believed to be susceptible to expressing Brachyury at some stage of the cancer in at least a subset of individuals with the cancer. In one aspect of this embodiment, the individual already has a cancer, but Brachyury is not detected in the cancer at the time the composition is first administered, meaning that the individual may have an earlier stage cancer in which Brachyury expression has not yet manifested, or in which Brachyury expression is not yet detectable in any event (i.e., Brachyury may or may not be expressed at a low level or in a small number of tumor cells, but is not yet readily detectable using standard detection methods). In some cases, the type of cancer may be known to have a high rate of metastatic progression, In this aspect, administration of the yeast-Brachyury immunotherapeutic composition prevents, delays or inhibits the development of Brachyury-expressing tumor cells in the patient's cancer, and therefore prevents, arrests, delays or inhibits metastatic processes that accompany Brachyury expression. In another aspect, the individual does not have cancer when the composition is administered. Such an individual may be "predisposed" or likely to develop cancer, perhaps because of family history or a genetic marker, or because the individual has shown signs of precancerous cells or lesions or has precancerous (premalignant) cells or lesions.

One embodiment of the invention relates to a method to inhibit tumor migration and/or to reduce, halt (arrest), reverse or prevent the metastatic progression of cancer in an individual who has cancer, or to reverse the development of metastatic events in a cancer. As discussed above, Brachyury promotes the epithelial-mesenchymal transition (EMT) in human tumor cells, conferring on tumor cells a mesenchymal phenotype, as well as migratory and invasive abilities, while attenuating tumor cell cycle progression. Therefore, the involvement of Brachyury in metastatic processes makes it an ideal target for the prevention or inhibition of metastatic processes, including arresting cancer at a pre-metastatic stage. Use of a yeast-Brachyury immunotherapeutic composition of the invention can be effective to prevent or treat metastatic cancer, including arresting progression of the cancer, in the face of escape (or attempted escape) of the cancer from traditional therapy, such as chemotherapy and radiation. The method includes the steps of administering to the individual who has cancer a yeast-Brachyury immunotherapeutic composition of the invention as described herein, including, but not limited to: (a) a yeast vehicle; and (b) a cancer antigen comprising at least one modified Brachyury antigen of the invention.

In one aspect, Brachyury is not detected in the individual's cancer at the time the composition is first administered. In general, when Brachyury is not detected in the individual's cancer, the individual may have an earlier stage cancer in which Brachyury expression has not yet manifested (e.g., stage I or stage II), or in which Brachyury expression is not yet detectable in any event (i.e., Brachyury may or may not be expressed at a low level or in a small number of tumor cells, but is not yet readily detectable using standard detection methods). In this aspect of the invention, the development of Brachyury-expressing tumor cells is prevented, delayed or inhibited by use of the yeast-Brachyury immunotherapeutic composition. As a result, tumor migration and/or other metastatic processes leading to metastatic progression of the tumor are prevented, delayed or inhibited and/or general arrest of tumor progression occurs in the individual.

In another aspect, Brachyury expression is or can be detected in the individual's cancer at the time the composition is first administered. The individual may have stage I, stage II, stage III, or stage IV cancer in this aspect of the invention. In this aspect, use of the yeast-Brachyury immunotherapeutic composition reduces, eliminates or slows or arrests the growth of tumors expressing Brachyury, which can result in reduction in tumor burden in the individual, inhibition of Brachyury-expressing tumor growth, and/or increased survival of the individual. The individual may experience an arrest, slowing or reversal in metastatic processes, improving survival and health of the patient, and furthermore, allowing other therapeutic protocols to treat the cancer.

Indeed, metastatic cancer can be associated with resistance, or increased resistance, to cancer therapies such as chemotherapy, radiation, or targeted cancer therapy, whereby the cancer "escapes" from the therapy or is simply less impacted by the therapy and progresses. Accordingly, there is a need to reduce or eliminate resistance to such therapies to improve or enhance the efficacy of the therapy and improve patient health and survival. Accordingly, one embodiment of the invention relates to a method to reduce or prevent chemotherapy-resistance, targeted cancer therapy-resistance, or radiation-resistance in a patient with cancer. The method comprises administering to an individual who has cancer and is receiving chemotherapy and/or radiation therapy for the cancer, a yeast-Brachyury immunotherapeutic composition as described herein, which may include a composition comprising: (a) a yeast vehicle; and (b) a cancer antigen comprising at least one modified Brachyury antigen of the invention. This method of the invention may also be used to treat resistance associated with other therapeutic treatments for cancer, including, but not limited to, targeted cancer therapy.

In one aspect of this embodiment, Brachyury is not detected in the individual's cancer at the time the composition is first administered. In this aspect, administration of a yeast-Brachyury immunotherapeutic composition prevents or inhibits the onset of resistance to chemotherapy or radiation therapy by inhibiting the development of Brachyury-expressing tumor cells in the cancer. In another aspect, Brachyury expression is detected in the individual's cancer at the time the composition is first administered. In this aspect, the individual may or may not already be experiencing resistance to chemotherapy or radiation. In either case, administration of the yeast-Brachyury immunotherapeutic composition of the invention prevents or inhibits the resistance to chemotherapy or radiation therapy or enhances the ability of the chemotherapy or radiation therapy to treat the individual, by reducing or eliminating Brachyury-expressing tumor cells in the patient.

Yet another embodiment of the invention relates to a method to treat chordoma by administering a yeast-Brachyury immunotherapy composition of the invention to an individual (subject) with chordoma. Chordoma is characterized by the expression of Brachyury and indeed, Brachyury is a distinguishing biomarker for this cancer, i.e., Brachyury expression is common to and a specific biomarker for all chordomas. This method of the invention therefore includes the step of administering to the individual who has chordoma, or the individual who is at risk of developing chordoma but in whom Brachyury-expressing cancer cells are not currently detected, a yeast-Brachyury immunotherapeutic composition as described herein, including, but not limited to: (a) a yeast vehicle; and (b) a cancer antigen comprising at least one modified Brachyury antigen of the invention. The subject to be treated with the immunotherapeutic composition of the present invention, can be a chordoma subject having a first occurrence of a non-resectable lesion (i.e., not able to be completely surgically removed) or a resectable lesion; a subject having a non-resectable, locally recurring lesion (i.e., locally recurring is a lesion that reappears in the vicinity of (at or near) the same place as an original or primary lesion that has been removed), whether first recurrence or not; a subject having oligometastatic disease as described below; or a subject having metastatic disease as described below. In one aspect, the subject may or may not have had previous radiation therapy, surgery and/or targeted drug therapy. In another aspect, the subject has a cancer lesion that has been previously irradiated. In one aspect, the subject has a cancer lesion that has not been previously irradiated. In one aspect, the subject is administered yeast-Brachyury immunotherapy, and additionally a cancer lesion is irradiated prior to, during, and/or after administration of yeast-Brachyury immunotherapy.

In one aspect of any of the methods described above, the individual, in addition to being administered a yeast-Brachyury composition of the present invention, is additionally treated with at least one other therapeutic compound or therapeutic protocol useful for the treatment of cancer, administered or performed prior to, sequentially with, concurrently with, and/or after the administration of the yeast-based immunotherapy composition of the invention. For example, in any of the embodiments regarding methods of the invention described herein, in one aspect, when the individual has cancer (regardless of the status of detectable Brachyury expression in tumor cells) the individual is being treated or has been treated with another therapy for cancer. Such therapy can include any of the therapeutic protocols or use of any therapeutic compound or agent described previously herein, including, but not limited to, chemotherapy or targeted cancer therapy or drug therapy (e.g., tyrosine kinase inhibitors, including, but not limited to, imatinib, sunitinib cetuximab, gefitinib, erlotinib, nilotinib, dasatinib, lapatinib and everolimus; STAT3 inhibitors, anthracyclines; cisplatins; alkylating agents; camptothecin analogues), radiation therapy (including, but not limited to, stand alone radiation therapy and adjuvant radiation therapy, especially hadron-based radiation therapy), surgical resection of a tumor, stem cell transfer, cytokine therapy, adoptive T cell transfer, and/or administration of a second immunotherapeutic composition. In the case of administration of a second immunotherapeutic composition, such compositions may include, but are not limited to, additional yeast-based immunotherapy, recombinant virus-based immunotherapy (viral vectors), cytokine therapy, immunostimulant therapy (including chemotherapy with immunostimulating properties), DNA vaccines, and other immunotherapy compositions.

Any of these additional agents or therapies can be administered or performed prior to the first dose of yeast-Brachyury immunotherapy composition or after the first dose is administered. In one embodiment, one or more therapies can be administered or performed in an alternating manner with the dosing of yeast-Brachyury immunotherapy composition, such as in a protocol in which the yeast-Brachyury composition is administered at prescribed intervals in between one or more consecutive doses of chemotherapy or other therapy. In one embodiment, the yeast-Brachyury immunotherapy composition is administered in one or more doses over a period of time prior to commencing additional therapies. In other words, the yeast-Brachyury immunotherapeutic composition is administered as a monotherapy for a period of time, and then an additional therapy is added (e.g., chemotherapy or radiation therapy), either concurrently with new doses of yeast-Brachyury immunotherapy, or in an alternating fashion with yeast-Brachyury immunotherapy. Alternatively or in addition, another therapy may be administered for a period of time prior to beginning administration of the yeast-Brachyury immunotherapy composition, and the concepts may be combined (e.g., surgical resection of a tumor, followed by monotherapy with yeast-Brachyury immunotherapy for several weeks, followed by alternating doses of chemotherapy or radiation therapy and yeast-Brachyury immunotherapy for weeks or months, optionally followed by monotherapy using yeast-Brachyury immunotherapy or another therapy, or by a new protocol of combinations of therapy provided sequentially, concurrently, or in alternating fashion). Various protocols for the treatment of cancer using yeast-Brachyury immunotherapy are contemplated by the invention, and these examples should be considered to be non-limiting examples of various possible protocols.

In one aspect, the second immunotherapeutic composition includes a second cancer antigen that does not include Brachyury antigen. For example, a second immunotherapeutic composition useful in combination with a yeast-Brachyury immunotherapeutic composition is a yeast-immunotherapeutic composition comprising another cancer antigen. Such cancer antigens may include, but are not limited to, carcinoembryonic antigen (CEA), point mutated Ras oncoprotein, MUC-1, EGFR, BCR-Abl, MART-1, MAGE-1, MAGE-3, GAGE, GP-100, MUC-2, normal and point mutated p53 oncoproteins, PSMA, tyrosinase, TRP-1 (gp75), NY-ESO-1, TRP-2, TAG72, KSA, CA-125, PSA, HER-2/neu/c-erb/B2, hTERT, p73, B-RAF, adenomatous polyposis *coli* (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, NGEP, modifications of such antigens, splice variants of such antigens, and epitope agonists of such antigens, as well as combinations of such antigens, and/or immunogenic domains thereof, modifications thereof, variants thereof, and/or epitope agonists thereof.

As used herein, to "treat" a cancer, or any permutation thereof (e.g., "treated for cancer", etc.) generally refers to administering a composition of the invention once the cancer has occurred (e.g., once the cancer has been diagnosed or detected in an individual), with at least one therapeutic goal of the treatment (as compared to in the absence of this treatment) including: ameliorating at least one symptom of cancer, such as by reducing tumor burden in the individual; inhibiting, reducing, decreasing, or diminishing tumor growth or the rate of tumor growth (tumor growth kinetics) in the individual; increasing or extending survival of the individual, which can include overall survival and/or progression free survival; improving tumor response rate, (i.e., as measured by RECIST and/or Choi, defined below); delaying, inhibiting, arresting or preventing the recurrence of the tumor; preventing, inhibiting, reversing or delaying development of tumor migration and/or tumor invasion of other tissues (metastatic cancer); arresting, preventing, inhibiting, reversing or delaying progression of the cancer in the individual; improving long term memory immune responses against the tumor antigen(s) expressed by the cancer; increasing the sensitivity of the lesions to radiation therapy, chemotherapy and/or targeted drug therapy; and/or improving the general health of the individual.

To "prevent" or "protect" from a cancer, or any permutation thereof (e.g., "prevention of cancer", etc.), generally refers to administering a composition of the invention before a cancer has occurred, or before a specific stage of cancer or tumor antigen expression in a cancer has occurred (e.g., before Brachyury expression is detected in the cancer), with at least one goal of the treatment (as compared to in the absence of this treatment) including: preventing or delaying the onset or development of cancer, or, should the cancer nonetheless occur after the treatment, at least improving the outcomes in the individual as compared to in the absence of the treatment, including, but not limited to, reducing tumor burden in the individual; inhibiting (reducing, decreasing, diminishing) tumor growth or the rate of tumor growth in the individual; increasing (extending) survival of the individual, which can include overall survival and/or progression free survival; improving tumor response rate, (i.e., as measured by RECIST and/or Choi, defined below); delaying, inhibiting, arresting or preventing the recurrence of the tumor; preventing, inhibiting, reversing or delaying development of tumor migration and/or tumor invasion of other tissues (metastatic cancer); arresting, preventing, inhibiting, reversing or delaying progression of the cancer in the individual; improving long term memory immune responses against the tumor antigens expressed by the cancer; increasing the sensitivity of the tumor to radiation therapy, chemotherapy and/or targeted drug therapy; and/or improving the general health of the individual.

In one embodiment of the invention, treatment with a yeast-based immunotherapy composition of the invention improves response rates in the subject, i.e., as measured by RECIST or Choi criteria. "RECIST" refers to Response Evaluation Criteria in Solid Tumors and is a set of published guidelines that define when tumors in cancer patients improve, stabilize or progress. A RECIST-defined response depends on changes in the size of target lesions, as determined by non-invasive imaging assessment. RECIST criteria were originally published in February 2000 by an international collaboration including the European Organization for Research and Treatment of Cancer (EORTC), National Cancer Institute (NCI) of the United States and the National Cancer Institute of Canada Clinical Trials Group. (Therasse et al., *J. Natl. Cancer Inst.* 2000, 92:205-216)) and were revised in 2009 as described in Eisenhauer et al., *Eur. J. Cancer,* 2009, 45:228-247. As described in Eisenhauer et al., supra, a "Complete Response" or CR is currently defined as a disappearance of all target lesions, with any pathological lymph nodes (target or non-target) having a reduction in short axis to <10 mm. A "Partial Response" or "PR" is currently defined as at least a 30% decrease in the sum of diameters of target lesions, taking as reference the baseline sum diameters. "Stable Disease" or "SD" is defined as neither sufficient shrinkage to qualify for PR nor sufficient increase to qualify for PD, taking as reference the smallest sum diameters while on study. A "Progressive Disease" or "PD" is defined as at least a 20% increase in the sum of diameters of target lesions, taking as reference the smallest sum on study. In addition, the sum must also demonstrate an absolute increase of at least 5 mm. The appearance of one or more new lesions is also considered to be progression. Additional criteria apply to non-target lesions as described in Eisenhauer et al. supra.

"Choi" criteria refers to a set of computed tomography response criteria originally described by Choi et al. (*J. Clin. Oncol.* 2007, 25(13):1753-1759) and evaluates a change in the size or in the density of target lesions as measured by CT. The Choi criteria also categorize patients using the CR, PR, SD and PD groupings. CR is defined as a disappearance of all lesions with no new lesions. PR is defined as a decrease in size >10% or a decrease in tumor attenuation >15% on CT, with no new lesions and no obvious progression of non-measurable disease. SD is defined as not meeting criteria for CR, PR or PD and no symptomatic deterioration attributed to tumor progression. PD is defined as an increase in tumor size >10% and does not meet criteria of PR by tumor attenuation on CT, and/or has new lesions.

The delivery (administration, immunization) of a yeast-Brachyury immunotherapeutic composition of the invention to a subject or individual can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, modified Brachyury antigen(s) and any other antigens, agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of a tumor). Suitable routes of administration will be apparent to those of skill in the art, depending on the type of cancer to be prevented or treated and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). In one aspect, a yeast-Brachyury immunotherapeutic composition of the invention is administered subcutaneously. In one aspect, the yeast-Brachyury immunotherapeutic composition is administered directly into a tumor milieu. In one aspect, a yeast-based immunotherapeutic composition of the invention is administered intrathecally.

In one aspect of the invention, a yeast-Brachyury immunotherapeutic composition is formulated for, and administered by, injection, e.g., by subcutaneous injection. In one aspect, the yeast-Brachyury immunotherapeutic composition is provided in a vialed suspension, with instructions for the proper handling, dosing, and administration to a subject. In one aspect, the yeast-Brachyury immunotherapeutic composition is provided as a vialed, lyophilized formulation, with instructions for the proper handling, resuspension, dosing, and administration to a subject. One advantage of the modified Brachyury antigens of the invention, and the subsequent reduction in the flocculation phenotype of the yeast expressing the antigen, is that administration of the yeast-Brachyury immunotherapy composition requires less effort on the part of the medical practitioner to ensure that the composition is properly suspended or resuspended in the vial and remains properly suspended during loading into the syringe and administration to the subject.

In general, a suitable single dose of a yeast-Brachyury immunotherapeutic composition of the present invention, is a dose that is capable of effectively providing a yeast vehicle and the modified Brachyury antigen to a given cell type, tissue, or region of the patient body in an amount effective to elicit an antigen-specific immune response against one or more tumor antigens or epitopes (e.g., Brachyury), when administered one or more times over a suitable time period. For example, in one embodiment, a single dose of a yeast-based composition of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Yeast Units (Y.U., which is $1 \times 10^6$ yeast cells or yeast cell equivalents) to about 100

Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). In one embodiment, doses include doses between 1 Y.U and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60 Y.U., 70 Y.U., or 80 Y.U. In one embodiment, the doses are administered at different sites on the individual but during the same dosing period. For example, a 40 Y.U. dose may be administered by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose. One Yeast Unit (Y.U.) is $1\times10^7$ yeast cells or yeast cell equivalents.

"Boosters" or "boosts" of an immunotherapeutic composition of the invention are administered, for example, when the immune response against the antigen has waned or as needed to provide an immune response or induce a memory response against a particular antigen or antigen(s). Boosters can be administered about 1, 2, 3, 4, 5, 6, 7, or 8 weeks apart, or monthly, bimonthly, quarterly, annually, and/or in a few or several year increments after the original administration, depending on the status of the individual being treated and the goal of the therapy at the time of administration (e.g., prophylactic, active treatment, maintenance). In one embodiment, an administration schedule is one in which doses of yeast-based immunotherapeutic composition are administered at least 1, 2, 3, 4, 5, 6, 7, 8, 9, 10, or more times over a time period of from weeks, to months, to years. In one embodiment, the doses are administered weekly or biweekly for 1, 2, 3, 4, 5, 6, 7, 8, 9, 10 or more doses, followed by biweekly or monthly doses as needed to achieve the desired preventative or therapeutic treatment for chordoma. In one embodiment, doses are administered biweekly for 1, 2, 3, 4, 5, 6, 7, 8, 9, 10 or more doses, followed by additional monthly doses until the desired preventative or therapeutic result is achieved. In one embodiment, doses are administered monthly for 1, 2, 3, 4, 5, 6, 7, 8, 9, 10 or more doses, followed by additional monthly doses or followed by doses delivered at different frequencies (e.g., quarterly) as needed to achieve the desired preventative or therapeutic treatment for the cancer. In all of the dosing protocols described herein, additional boosters can then be given at similar or longer intervals (e.g., months or years) as a maintenance or remission therapy, if desired. In one aspect, boosters are administered for long term maintenance therapy (i.e., after the main course of therapy is completed, with an intention of preventing or delaying recurrence of disease, or with the intention of maintaining disease stabilization In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect utilizing the invention include humans, non-human primates, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin, W. Orenstein, and P. Offit, eds., Fifth Edition (2008).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN®s have been generally described (see, e.g., U.S. Pat. No. 5,830,463). Certain yeast-based immunotherapy compositions, and methods of making and generally using the same, are also described in detail, for example, in U.S. Pat. No. 5,830,463, U.S. Pat. No. 7,083,787, U.S. Pat. No. 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic, physiological, chemical, or other processes of a cell, a tissue, or an organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

General reference to a protein or polypeptide used in the present invention includes full-length proteins, near full-length proteins (defined above), or any fragment, domain (structural, functional, or immunogenic), conformational epitope, or a homologue or variant of a given protein. A fusion protein may also be generally referred to as a protein or polypeptide. An isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" or "variant" is used to refer to a protein or peptide which differs from a reference protein or peptide (i.e., the "prototype" or "wild-type" protein) by minor modifications to the reference protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue or variant can have enhanced, decreased, or substantially similar properties as compared to the reference protein or peptide. A homologue or variant can include an agonist of a protein or an antagonist of a protein. Homologues or variants can be produced using techniques known in the art for the production of proteins including, but not limited to, direct modifications to the isolated reference protein, direct protein synthesis, or modifications to the nucleic acid sequence encoding the protein using, for example, classic or recombinant DNA techniques to effect random or targeted mutagenesis, resulting in the encoding of a protein variant. In addition, naturally occurring variants of a reference protein may exist (e.g., isoforms, allelic variants, or other natural variants that may occur from individual to individual) and may be isolated, produced and/or utilized in the invention.

A homologue or variant of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 86% identical, or at least about 87% identical, or at least about 88% identical, or at least about 89% identical, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein (e.g., an amino acid sequence specified herein, or the amino acid sequence of a specified protein). In one embodiment, the homologue or variant comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the amino acid sequence of the reference protein.

As used herein, unless otherwise specified, reference to a percent (%) identity refers to an evaluation of homology which is performed using: (1) a Basic Local Alignment Search Tool (BLAST) basic homology search using blastp for amino acid searches and blastn for nucleic acid searches with standard default parameters, wherein the query sequence is filtered for low complexity regions by default (such as described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." *Nucleic Acids Res.* 25:3389-3402, incorporated herein by reference in its entirety); (2) a BLAST alignment of two sequences (e.g., using the parameters described below); (3) and/or PSI-BLAST with the standard default parameters (Position-Specific Iterated BLAST. It is noted that due to some differences in the standard parameters between Basic BLAST and BLAST for two sequences, two specific sequences might be recognized as having significant homology using the BLAST program, whereas a search performed in Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST as described in Tatusova and Madden, (1999), "Blast 2 sequences—a new tool for comparing protein and nucleotide sequences", FEMS Microbiol Lett. 174:247-250, incorporated herein by reference in its entirety. Such a sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST sequence alignment for two sequences is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome or a segment of the genome containing more than one gene, in which the nucleic acid molecule is found in nature. An isolated nucleic acid molecule can include a complete gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule may also include portions of a gene. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a plasmid useful for transfecting yeast. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell, such as a yeast.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the production of an improved yeast-Brachyury immunotherapeutic composition.

In this experiment, yeast (*Saccharomyces cerevisiae*) were engineered to express a human Brachyury antigen that is a near-full-length Brachyury protein comprising the T cell epitope WLLPGTSTV (SEQ ID NO:9), which is an agonist epitope and further comprising a deletion of the T box DNA binding domain. The native Brachyury T cell epitope, present in SEQ ID NO:4 or 6, for example, is WLLPGTSTL (SEQ ID NO:8). The human Brachyury agonist antigen was expressed under the control of the copper-inducible promoter, CUP1, producing a yeast-Brachyury immunotherapy composition. More particularly, a Brachyury agonist antigen that is also a modified Brachyury antigen according to the present invention was produced as a single polypeptide represented by SEQ ID NO:13. The amino acid sequence of SEQ ID NO:13 differs from the amino acid sequence of the human Brachyury protein represented by SEQ ID NO:4 (an unmodified Brachyury antigen) by: (1) a deletion of positions 198-222 (i.e., positions 198-222 of SEQ ID NO:4 are not present in SEQ ID NO:13); and (2) a substitution of the amino acid (leucine) located at position 254 in SEQ ID NO:4 (and located at position 229 of SEQ ID NO:13) with a valine. In other words, SEQ ID NO:13 is a single polypeptide consisting of positions 1-197 of SEQ ID NO:4 fused directly to positions 223-435 of SEQ ID NO:4, and including an amino acid modification (at position 229 of SEQ ID NO:13 which corresponds to position 254 of SEQ ID NO:4) that results in the introduction of an agonist epitope into SEQ ID NO:13. The leucine to valine substitution at position 254 (with respect to SEQ ID NO:4) creates a T cell agonist epitope in SEQ ID NO:13 at positions 221-229 of SEQ ID NO:13, that, without being bound by theory, is believed to induce enhanced T cell responses against Brachyury as compared to the wild-type epitope (positions 246 to 254 of SEQ ID NO:4). This agonist epitope is also represented herein by SEQ ID NO:6. The modified Brachyury antigen represented by SEQ ID NO:13 has disrupted DNA binding ability and yeast expressing the antigen have a reduced flocculation phenotype, as compared to the Brachyury protein of SEQ ID NO:4, and additionally contains the agonist epitope to enhance T cell responses against the native Brachyury when this construct is administered to a subject in a yeast-Brachyury immunotherapeutic.

SEQ ID NO:15 is a fusion protein comprising the modified Brachyury protein of SEQ ID NO:13 (actually positions 2-410 of SEQ ID NO:13, since the N-terminal methionine of SEQ ID NO:13 is removed to accommodate the addition of an N-terminal peptide described below). SEQ ID NO:15 is a single polypeptide with the following sequence elements fused in frame from N- to C-terminus: (1) an N-terminal peptide to impart resistance to proteasomal degradation and stabilize expression in yeast (positions 1-6 of SEQ ID NO:15, the amino acid sequence of which is also represented herein by SEQ ID NO:16); (2) a human Brachyury antigen consisting of positions 2-197 and 223-435 of SEQ ID NO:4 and further containing a substitution of a valine for the leucine at position 254 of SEQ ID NO:4, which can also be described as positions 2-410 of SEQ ID NO:13 (positions 7-415 of SEQ ID NO:15); and (3) a hexahistidine tag (positions 416-421 of SEQ ID NO:15). The amino acid sequence of SEQ ID NO:15 and the amino acid sequence of positions 2-410 of SEQ ID NO:13 is encoded by the polynucleotide sequence of SEQ ID NO:14. A yeast-based immunotherapy composition expressing this fusion protein is also referred to herein as GI-6306.

To produce the GI-6306 yeast immunotherapy composition, briefly, a DNA sequence encoding a human Brachyury protein having the amino acid sequence of SEQ ID NO:13 was synthesized, amplified using PCR, and then inserted at EcoRI and SpeI cloning sites behind the CUP1 promoter (vector pGI-100) in a yeast 2 µm expression vector. Nucleotide sequences encoding the N-terminal stabilization peptide, MADEAP (SEQ ID NO:16) and a C-terminal hexahistidine peptide were also added to the plasmid vector to encode the complete fusion protein represented by SEQ ID NO:15. The resulting plasmids were transformed into DH5α for plasmid storage, and into *Saccharomyces cerevisiae* W303α for production of the yeast-Brachyury immunotherapeutic compositions.

Transformation into *Saccharomyces cerevisiae* was performed by lithium acetate/polyethylene glycol transfection, and primary transfectants were selected on solid agar minimal plates lacking Uracil (UDA; uridine dropout agar). These primary transformant colonies were selected by re-streaking individual colonies on agar plates lacking both uridine and leucine (ULDA); followed by 4 days of growth at 30° C. to ensure clonal purity and to establish a steady state of high Brachyury plasmid copy number within the yeast cells.

Liquid starter cultures lacking uridine and leucine (UL4aa) were inoculated using colonies from the ULDA plates and were grown for 20 h at 30° C. with rotary shaking at 250 rpm. These primary cultures were then used to inoculate final cultures of the same UL4aa formulation.
Recipe for UL4aa liquid media (per liter):
25 grams (g) glucose
10 g yeast nitrogen base containing ammonium sulfate
0.08 g adenine
0.16 g tryptophan
0.16 g histidine In initial experiments to evaluate yeast-Brachyury immunotherapeutic compositions under the control of the CUP1-driven copper-inducible promoter, yeast-Brachyury expression was initiated in final cultures by the addition of 0.375 mM copper sulfate after the yeast-Brachyury culture reached a density of approximately 2 Y.U./ml, and induction was continued for 3 h at 30° C. The cells from each culture were then harvested, washed in PBS, and heat-killed at 56° C. for 1 hour in PBS.

After heat-kill of the cultures, the cells were washed three times in PBS. Total protein content was measured by a TCA precipitation/nitrocellulose binding assay and the Brachyury antigen expression was evaluated by Western blot using an anti-his tag monoclonal antibody and an anti-Brachyury antibody (Abcam, Cambridge, Mass.). The Brachyury antigen content of the yeast cells was quantified using semi-quantitative digital imaging of the Western blot, with interpolation of Brachury antigen band intensity/signal from yeast lysates onto standard curves containing known quantities of a recombinant purified his-tagged antigen.

The results of the initial expression experiments are shown in FIG. 1 and demonstrated that GI-6306 expressed the fusion protein (SEQ ID NO:15) comprising the modified Brachyury agonist antigen (positions 2-410 of SEQ ID NO:13) at high levels (16,438 ng/YU). This expression level is comparable to expression of a fusion protein comprising an unmodified Brachyury antigen (positions 2-435 of SEQ ID NO:4) expressed by the yeast immunotherapy composition known as GI-6301 (16,787 ng/YU; see FIG. 1). Expression of the modified Brachyury agonist antigen by GI-6306 was notably higher than the expression of a Brachyury agonist antigen that contained the same agonist point mutation as SEQ ID NO:13, but that did not contain the deletion of the DNA binding domain that is present in SEQ ID NO:13 (the yeast immunotherapy composition known as GI-6305, which expresses an amino acid sequence of positions 2-435 of SEQ ID NO:4, except for the substitution of a valine for the leucine at position 254 with respect to SEQ ID NO:4) (see FIG. 1, 10,862 ng/YU). Accordingly, abrogating the DNA binding activity of Brachyury (e.g., via deletion of DNA binding residues) appeared to significantly enhance expression of the Brachyury agonist antigen.

Figure 2:
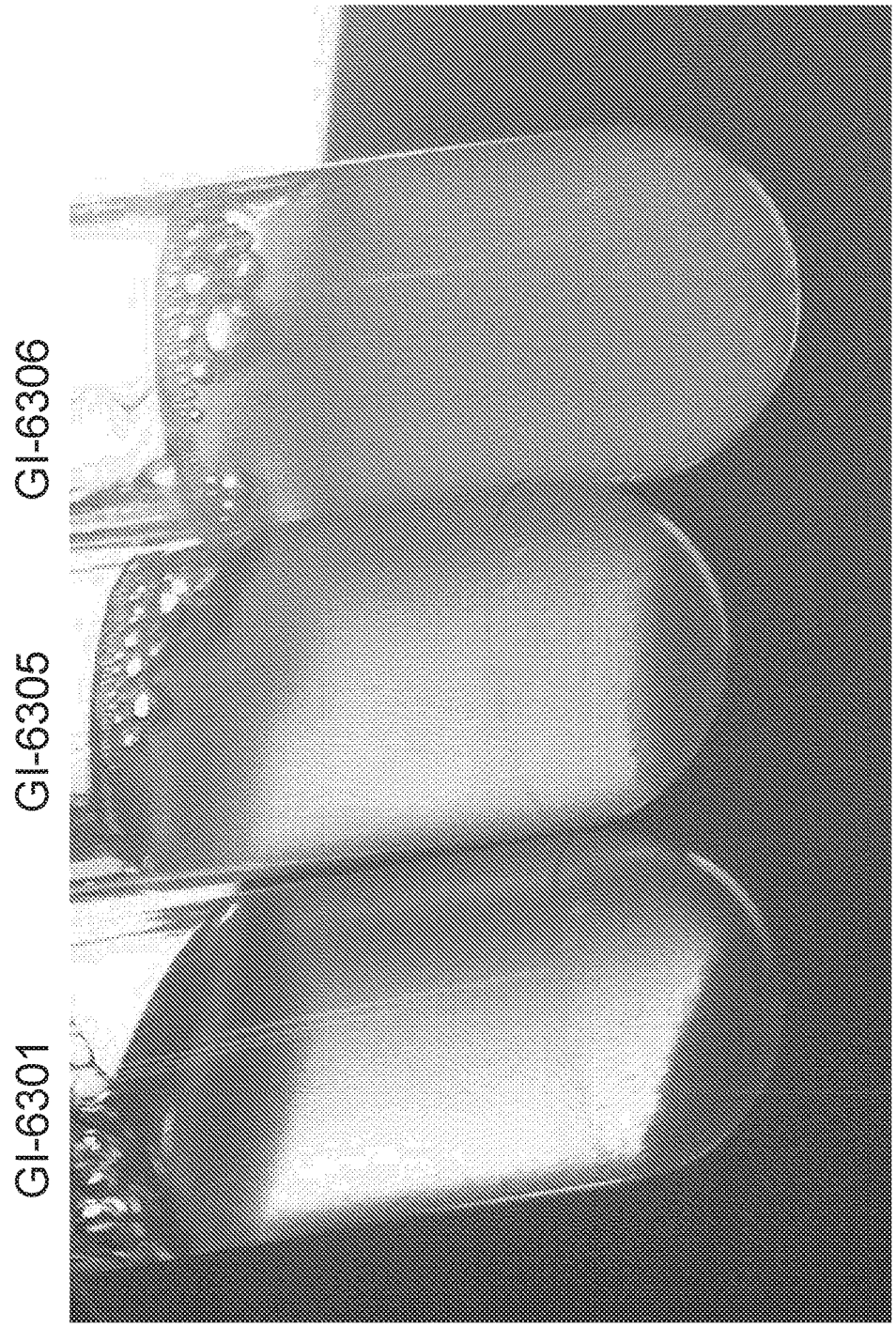
FIG. 2 is a digital image showing that the yeast-Brachyury immunotherapeutic composition known as GI-6306 displays a reduced flocculation phenotype compared to yeast-Brachyury immunotherapeutic compositions GI-6301 and GI-6305.

Cultures of the yeast-Brachyury immunotherapy products described above (GI-6301, GI-6305 and GI-6306) were also evaluated for flocculation characteristics based on visual inspection of settling. As shown in FIG. 2, the yeast-Brachyury composition GI-6306 is notably less flocculated than either of GI-6301 or GI-6305.

Example 2

The following example describes a phase 1 clinical trial in subjects with Brachyury-positive cancer.

An open-label, sequential dose-escalation, phase 1 clinical trial has been initiated using the yeast-Brachyury immunotherapy composition known as GI-6306 or another yeast-Brachyury immunotherapy composition as described herein. Under this clinical trial protocol, 9-18 cancer patients (3-6 patients per dose cohort) are administered the yeast-Brachyury immunotherapy composition in a sequential dose cohort escalation protocol utilizing dose ranges of 4 Y.U. (1 Y.U.×4 sites, meaning that 1 Y.U. of the immunotherapy composition is administered at 4 different sites on the body of the patient each visit), 16 Y.U. (4 Y.U.×4 sites), 40 Y.U. (10 Y.U.×4 sites) or 80 Y.U. (20 Y.U.×4 sites), administered subcutaneously. The immunotherapy composition is administered at 2 week intervals for a total of 7 visits (~3 months), and then monthly thereafter until the patients meet off-study criteria. An expansion cohort of patients (n=10) at maximum tolerated dose (MTD) or the observed best dose are selected for additional study. The results are monitoring safety and tolerability as a primary endpoint, and in the expanded cohort, whether a significant change in T cell precursors is detectable as measured by an increase in Brachyury-specific T cells in ELISpot assay and proliferation in response to Brachyury protein (e.g., Brachyury-specific $CD8^+$ or $CD4^+$ T cells emerging or expanding on treatment). As secondary endpoints, clinical benefit, such as progression-free survival, clinical radiographic response, reduction in serum markers, and/or reduction in circulating tumor cells is measured, as well as parameters of general immune activation, including frequency of immune cell subsets in peripheral blood ($CD8^+$ memory/effector T cells, $CD4^+$ memory/effector T cells, Tregs, NK cells, DCs) and changes in serum levels of cytokines (e.g., IFN-γ, IL-10, IL-12, IL-2, IL-4, TGF-β, etc.).

The immunotherapy composition, including GI-6306 is expected to be safe and well-tolerated with no significant toxicities. In addition, the immunotherapy composition is expected to produce treatment-emergent Brachyury-specific T cell responses or an improvement in pre-existing Brachyury-specific baseline T cell responses in at least some or a majority of patients. Some patients are also expected to have stabilized disease.

In an additional study or an expansion of this study, a yeast-Brachyury immunotherapeutic composition disclosed herein is administered to an additional cohort of patients, utilizing the maximum tolerated dose or observed best dose determined above, and the same primary and secondary endpoints are measured.

Example 3

The following example describes a phase 2 clinical trial using yeast-Brachyury immunotherapeutic compositions described herein.

A randomized phase 2 clinical trial in patients with breast cancer is run using a yeast-Brachyury immunotherapeutic composition as described in Example 1. At least 100 or more subjects with Stage I, II or III Brachyury-positive breast cancer are enrolled. Subject inclusion criteria can include subjects with Grade 1, 2 or 3 cancers. Subject including criteria can also include subjects with "triple negative"

breast cancer (cancers that are negative for each of estrogen receptor (ER), progesterone receptor (PR) and HER2). Subject inclusion criteria can also include patients with lymph node-negative cancer.

The trial is run as a double-blind or open-label, placebo-controlled, multi-center trial. All patients receive standard of care therapy with treatment arm patients receiving several serial injections of yeast-Brachyury immunotherapeutic composition during treatment. The primary endpoint is recurrence free survival or overall survival. Additional endpoints can include antigen-specific T cell responses (e.g., Brachyury-specific CD8+ T cells emerging or expanding on treatment), maintenance of lymph node negativity, progression to metastases, and Brachyury expression in tumor cells.

The yeast-Brachyury immunotherapeutic composition is expected to be safe and well-tolerated with no significant toxicities. In addition, the yeast-Brachyury immunotherapeutic composition is expected to produce treatment-emergent Brachyury-specific T cell responses and/or an improvement in pre-existing Brachyury-specific baseline T cell responses in at least some or a majority of patients. Some or a majority of patients are also expected to have stabilized disease, maintain lymph node negativity, and/or prevention, reduction or arrest in metastatic progression.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A yeast-Brachyury immunotherapeutic composition, wherein the immunotherapeutic composition comprises:
   a) a yeast;
   b) at least one modified Brachyury antigen expressed by the yeast, wherein the modified Brachyury antigen has an amino acid sequence comprising SEQ ID NO:10, positions 2-410 of SEQ ID NO:10, SEQ ID NO:13, or positions 2-410 of SEQ ID NO:13; and wherein the modified Brachyury antigen has an amino acid sequence that differs from a wild-type Brachyury amino acid sequence of SEQ ID NO:4 by a deletion of positions 198 through 222 of the wild-type Brachyury, wherein the Brachyury antigen has a disrupted DNA binding site as compared to the wild-type Brachyury.

2. The yeast-Brachyury immunotherapeutic composition of claim 1, wherein the yeast have a reduced flocculation phenotype as compared to a yeast expressing a wild-type Brachyury.

3. The yeast-Brachyury immunotherapeutic composition of claim 1, wherein the modified Brachyury antigen is a fusion protein having an amino acid sequence comprising SEQ ID NO:12 or SEQ ID NO:15.

4. The yeast-Brachyury immunotherapeutic composition of claim 1, wherein the composition is formulated in a pharmaceutically acceptable excipient suitable for administration to a subject.

5. A yeast-Brachyury immunotherapeutic composition comprising:

a) a whole, inactivated yeast; and b) a Brachyury fusion protein comprising the amino acid sequence of positions 2-410 of SEQ ID NO:10;

wherein the Brachyury fusion protein was expressed by the yeast; and wherein the composition elicits a Brachyury-specific T cell response.

6. A yeast-Brachyury immunotherapeutic composition comprising:

a) a whole, inactivated yeast; and b) a Brachyury fusion protein comprising the amino acid sequence of positions 2-410 of SEQ ID NO:13;

wherein the Brachyury fusion protein was expressed by the yeast; and wherein the composition elicits a Brachyury-specific T cell response.

7. A method to treat a cancer that expresses Brachyury, comprising administering to a subject with a cancer that expresses Brachyury a yeast-Brachyury immunotherapeutic composition of claim 1.

8. A method to treat the metastatic progression of cancer in an individual who has cancer, wherein the cancer is undergoing metastatic progression, comprising administering to the individual the immunotherapeutic composition of claim 1.

9. A method to treat chemotherapy-resistance or radiation-resistance of tumor cells in a patient with cancer, comprising administering to an individual who has cancer and is receiving chemotherapy and/or radiation therapy an immunotherapeutic composition of claim 1.

10. A method to treat a B-cell lymphoma associated with Epstein Barr Virus (EBV) infection, comprising administering to an individual with an EBV infection a yeast-Brachyury immunotherapeutic composition of claim 1.

\* \* \* \* \*